United States Patent
Schneider et al.

(10) Patent No.: US 9,549,848 B2
(45) Date of Patent: Jan. 24, 2017

(54) CORNEAL IMPLANT INSERTERS AND METHODS OF USE

(75) Inventors: Ned Schneider, Aliso Viejo, CA (US); Alan Ngoc Le, Lake Forest, CA (US); Jon Dishler, Cherry Hills Village, CO (US)

(73) Assignee: REVISION OPTICS, INC., Lake Forest, CA (US)

( * ) Notice: Subject to any disclaimer, the term of this patent is extended or adjusted under 35 U.S.C. 154(b) by 451 days.

(21) Appl. No.: 13/619,955

(22) Filed: Sep. 14, 2012

(65) Prior Publication Data

US 2013/0253527 A1 Sep. 26, 2013

Related U.S. Application Data

(63) Continuation-in-part of application No. 13/411,425, filed on Mar. 2, 2012, now Pat. No. 8,540,727, which is a continuation of application No. 11/692,835, filed on Mar. 28, 2007, now Pat. No. 8,162,953.

(60) Provisional application No. 61/535,744, filed on Sep. 16, 2011.

(51) Int. Cl.
    *A61F 9/00* (2006.01)
    *A61F 9/007* (2006.01)
    *A61F 2/14* (2006.01)

(52) U.S. Cl.
    CPC .............. *A61F 9/007* (2013.01); *A61F 2/148* (2013.01)

(58) Field of Classification Search
    CPC ...... A61F 2/146; A61F 2/1662; A61F 2/1675; A61F 2/1678; A61F 9/00736
    See application file for complete search history.

(56) References Cited

U.S. PATENT DOCUMENTS

| | | |
|---|---|---|
| 2,714,721 A | 8/1955 | Stone, Jr. |
| 3,091,328 A | 5/1963 | Leonardos |
| 3,168,100 A | 2/1965 | Rich |
| 3,343,657 A | 9/1967 | Speshyock |
| 3,379,200 A | 4/1968 | Pennell |
| 3,482,906 A | 12/1969 | Volk |
| 3,743,337 A | 7/1973 | Crary |
| 3,770,113 A | 11/1973 | Thomas |
| 3,879,076 A | 4/1975 | Barnett |
| 3,950,315 A | 4/1976 | Cleaver |

(Continued)

FOREIGN PATENT DOCUMENTS

| | | | | |
|---|---|---|---|---|
| CH | WO 2011069907 A1 | * | 6/2011 | ........... A61F 2/0095 |
| DE | 3208729 A1 | | 9/1983 | |

(Continued)

OTHER PUBLICATIONS

Dishler et al.; U.S. Appl. No. 13/854,588 entitled "Small Diameter Corneal Inlays," filed Apr. 1, 2013.

(Continued)

*Primary Examiner* — Ashley Fishback
(74) *Attorney, Agent, or Firm* — Shay Glenn LLP

(57) ABSTRACT

Devices that are adapted to insert corneal implants onto corneal tissue. Methods of using the devices include inserting the corneal implant into a pocket created in the cornea. Methods of use also include inserting the corneal implant onto corneal tissue after a flap has been created in the cornea. The devices can be adapted to deliver fluid to an implant holding space to at least assist in the deployment of the implant from the holding space and onto corneal tissue.

15 Claims, 23 Drawing Sheets

(56) References Cited

U.S. PATENT DOCUMENTS

| | | |
|---|---|---|
| 3,996,627 A | 12/1976 | Deeg et al. |
| 4,030,480 A | 6/1977 | Meyer |
| 4,037,604 A | 7/1977 | Newkirk |
| 4,039,827 A | 8/1977 | Zdrok et al. |
| 4,065,816 A | 1/1978 | Sawyer |
| 4,071,272 A | 1/1978 | Drdlik |
| 4,093,291 A | 6/1978 | Schurgin |
| 4,136,406 A | 1/1979 | Norris |
| 4,157,718 A | 6/1979 | Baehr |
| 4,184,491 A | 1/1980 | McGannon |
| 4,194,814 A | 3/1980 | Fischer et al. |
| 4,238,524 A | 12/1980 | LaLiberte et al. |
| 4,257,521 A | 3/1981 | Poler |
| 4,268,133 A | 5/1981 | Fischer et al. |
| 4,326,306 A | 4/1982 | Poler |
| 4,357,940 A | 11/1982 | Muller |
| 4,392,569 A | 7/1983 | Shoup |
| 4,418,991 A | 12/1983 | Breger |
| 4,423,809 A | 1/1984 | Mazzocco |
| 4,428,746 A | 1/1984 | Mendez |
| 4,452,235 A | 6/1984 | Reynolds |
| 4,466,705 A | 8/1984 | Michelson |
| 4,490,860 A | 1/1985 | Rainin |
| 4,504,982 A | 3/1985 | Burk |
| 4,521,210 A | 6/1985 | Wong |
| 4,525,044 A | 6/1985 | Bauman |
| 4,545,478 A | 10/1985 | Waldman |
| 4,554,115 A | 11/1985 | Neefe |
| 4,554,918 A | 11/1985 | White |
| 4,565,198 A | 1/1986 | Koeniger |
| 4,573,998 A | 3/1986 | Mazzocco |
| 4,580,882 A | 4/1986 | Nuchman et al. |
| 4,586,929 A | 5/1986 | Binder |
| 4,604,087 A | 8/1986 | Joseph |
| 4,607,617 A | 8/1986 | Choyce |
| 4,616,910 A | 10/1986 | Klein |
| 4,618,227 A | 10/1986 | Bayshore |
| 4,619,256 A | 10/1986 | Horn |
| 4,624,664 A | 11/1986 | Peluso et al. |
| 4,624,669 A | 11/1986 | Grendahl |
| 4,640,595 A | 2/1987 | Volk |
| 4,646,720 A | 3/1987 | Peyman et al. |
| 4,655,774 A | 4/1987 | Choyce |
| 4,662,370 A | 5/1987 | Hoffmann et al. |
| 4,663,358 A | 5/1987 | Hyon et al. |
| 4,671,276 A | 6/1987 | Reynolds |
| 4,676,792 A | 6/1987 | Praeger |
| 4,697,697 A | 10/1987 | Graham et al. |
| 4,702,244 A | 10/1987 | Mazzocco |
| 4,709,697 A | 12/1987 | Muller |
| 4,721,124 A | 1/1988 | Tuerkheimer et al. |
| 4,726,367 A | 2/1988 | Shoemaker |
| 4,750,901 A | 6/1988 | Molteno |
| 4,762,496 A | 8/1988 | Maloney et al. |
| 4,766,895 A | 8/1988 | Reynolds |
| 4,769,033 A | 9/1988 | Nordan |
| 4,772,283 A | 9/1988 | White |
| 4,778,462 A | 10/1988 | Grendahl |
| 4,798,609 A | 1/1989 | Grendahl |
| 4,806,382 A | 2/1989 | Goldberg et al. |
| 4,836,201 A | 6/1989 | Patton et al. |
| 4,840,175 A | 6/1989 | Peyman |
| 4,842,599 A | 6/1989 | Bronstein |
| 4,844,242 A | 7/1989 | Chen et al. |
| 4,851,003 A | 7/1989 | Lindstrom |
| 4,860,885 A | 8/1989 | Kaufman et al. |
| 4,865,552 A | 9/1989 | Maloney et al. |
| 4,886,488 A | 12/1989 | White |
| 4,888,016 A | 12/1989 | Langerman |
| 4,897,981 A | 2/1990 | Beck |
| 4,911,715 A | 3/1990 | Kelman |
| 4,919,130 A | 4/1990 | Stoy et al. |
| 4,923,467 A | 5/1990 | Thompson |
| 4,934,363 A | 6/1990 | Smith et al. |
| 4,936,825 A | 6/1990 | Ungerleider |
| 4,946,436 A | 8/1990 | Smith |
| 4,955,903 A | 9/1990 | Sulc et al. |
| 4,968,296 A | 11/1990 | Ritch et al. |
| 4,971,732 A | 11/1990 | Wichterle |
| 4,976,719 A | 12/1990 | Siepser |
| 5,019,084 A | 5/1991 | Aysta et al. |
| 5,019,098 A | 5/1991 | Mercier |
| 5,022,414 A | 6/1991 | Muller |
| 5,030,230 A | 7/1991 | White |
| 5,041,081 A | 8/1991 | Odrich |
| 5,063,942 A | 11/1991 | Kilmer et al. |
| 5,071,276 A | 12/1991 | Nielsen et al. |
| 5,073,163 A | 12/1991 | Lippman |
| 5,092,837 A | 3/1992 | Ritch et al. |
| 5,098,444 A | 3/1992 | Feaster |
| 5,108,428 A | 4/1992 | Capecchi et al. |
| 5,112,350 A | 5/1992 | Civerchia et al. |
| 5,123,905 A | 6/1992 | Kelman |
| 5,123,912 A | 6/1992 | Kaplan et al. |
| 5,123,921 A | 6/1992 | Werblin et al. |
| 5,139,518 A | 8/1992 | White |
| 5,163,934 A | 11/1992 | Munnerlyn |
| 5,171,213 A | 12/1992 | Price, Jr. |
| 5,173,723 A | 12/1992 | Volk |
| 5,178,604 A | 1/1993 | Baerveldt et al. |
| 5,180,362 A | 1/1993 | Worst et al. |
| 5,181,053 A | 1/1993 | Brown |
| 5,188,125 A | 2/1993 | Kilmer et al. |
| 5,190,552 A | 3/1993 | Kelman |
| 5,192,317 A | 3/1993 | Kalb |
| 5,196,026 A | 3/1993 | Barrett et al. |
| 5,211,660 A | 5/1993 | Grasso |
| 5,225,858 A | 7/1993 | Portney |
| 5,229,797 A | 7/1993 | Futhey et al. |
| 5,244,799 A | 9/1993 | Anderson |
| 5,258,042 A | 11/1993 | Mehta |
| 5,270,744 A | 12/1993 | Portney |
| 5,273,750 A | 12/1993 | Homiger et al. |
| 5,282,851 A | 2/1994 | Jacob-LaBarre |
| 5,300,020 A | 4/1994 | L'Esperance, Jr. |
| 5,300,116 A | 4/1994 | Chirila et al. |
| 5,312,413 A | 5/1994 | Eaton et al. |
| 5,318,044 A | 6/1994 | Kilmer et al. |
| 5,318,046 A | 6/1994 | Rozakis |
| 5,318,047 A | 6/1994 | Davenport et al. |
| 5,336,261 A | 8/1994 | Barrett et al. |
| 5,338,291 A | 8/1994 | Speckman et al. |
| 5,344,448 A | 9/1994 | Schneider et al. |
| 5,346,464 A | 9/1994 | Camras |
| 5,370,607 A | 12/1994 | Memmen |
| 5,372,577 A | 12/1994 | Ungerleider |
| 5,385,582 A | 1/1995 | Ommaya |
| 5,391,201 A | 2/1995 | Barrett et al. |
| 5,397,300 A | 3/1995 | Baerveldt et al. |
| 5,405,384 A | 4/1995 | Silvestrini |
| 5,428,412 A | 6/1995 | Stoyan |
| 5,433,701 A | 7/1995 | Rubinstein |
| 5,454,796 A | 10/1995 | Krupin |
| 5,458,819 A | 10/1995 | Chirila et al. |
| 5,467,149 A | 11/1995 | Morrison et al. |
| 5,474,562 A | 12/1995 | Orchowski et al. |
| 5,476,445 A | 12/1995 | Baerveldt et al. |
| 5,487,377 A | 1/1996 | Smith et al. |
| 5,489,301 A | 2/1996 | Barber |
| 5,493,350 A | 2/1996 | Seidner |
| 5,502,518 A | 3/1996 | Lieberman |
| 5,512,220 A | 4/1996 | Roffman et al. |
| 5,520,631 A | 5/1996 | Nordquist et al. |
| 5,521,656 A | 5/1996 | Portney |
| 5,530,491 A | 6/1996 | Baude et al. |
| 5,533,997 A | 7/1996 | Ruiz |
| 5,570,142 A | 10/1996 | Lieberman |
| 5,591,185 A | 1/1997 | Kilmer et al. |
| 5,598,234 A | 1/1997 | Blum et al. |
| 5,616,148 A | 4/1997 | Eagles et al. |
| 5,620,450 A | 4/1997 | Eagles et al. |
| 5,628,794 A | 5/1997 | Lindstrom |
| 5,630,810 A | 5/1997 | Machat |
| 5,634,943 A | 6/1997 | Villain et al. |

(56) References Cited

U.S. PATENT DOCUMENTS

| | | |
|---|---|---|
| 5,643,276 A | 7/1997 | Zaleski |
| 5,657,108 A | 8/1997 | Portney |
| 5,682,223 A | 10/1997 | Menezes et al. |
| 5,684,560 A | 11/1997 | Roffman et al. |
| 5,715,031 A | 2/1998 | Roffman et al. |
| 5,716,633 A | 2/1998 | Civerchia |
| 5,722,948 A | 3/1998 | Gross |
| 5,722,971 A | 3/1998 | Peyman |
| 5,728,155 A | 3/1998 | Anello et al. |
| 5,732,990 A | 3/1998 | Yavitz et al. |
| 5,752,928 A | 5/1998 | de Roulhac et al. |
| 5,755,785 A | 5/1998 | Rowsey et al. |
| 5,766,181 A | 6/1998 | Chambers et al. |
| 5,772,667 A | 6/1998 | Blake |
| 5,779,711 A | 7/1998 | Kritzinger et al. |
| 5,785,674 A | 7/1998 | Mateen |
| 5,800,442 A | 9/1998 | Wolf et al. |
| 5,800,529 A | 9/1998 | Brauker et al. |
| 5,805,260 A | 9/1998 | Roffman et al. |
| 5,810,833 A | 9/1998 | Brady et al. |
| 5,817,115 A | 10/1998 | Nigam |
| 5,824,086 A | 10/1998 | Silvestrini |
| 5,847,802 A | 12/1998 | Menezes et al. |
| 5,855,604 A | 1/1999 | Lee |
| 5,860,984 A | 1/1999 | Chambers et al. |
| 5,872,613 A | 2/1999 | Blum et al. |
| 5,873,889 A | 2/1999 | Chin |
| 5,876,439 A | 3/1999 | Lee |
| 5,888,243 A | 3/1999 | Silvestrini |
| 5,893,719 A | 4/1999 | Radow |
| 5,913,898 A | 6/1999 | Feingold |
| 5,919,185 A | 7/1999 | Peyman |
| 5,928,245 A | 7/1999 | Wolf et al. |
| 5,929,968 A | 7/1999 | Cotie et al. |
| 5,929,969 A | 7/1999 | Roffman |
| 5,935,140 A | 8/1999 | Buratto |
| 5,941,583 A | 8/1999 | Raimondi |
| 5,944,752 A | 8/1999 | Silvestrini |
| 5,945,498 A | 8/1999 | Hopken et al. |
| 5,964,748 A | 10/1999 | Peyman |
| 5,964,776 A | 10/1999 | Peyman |
| 5,968,065 A | 10/1999 | Chin |
| 5,976,150 A | 11/1999 | Copeland |
| 5,976,168 A | 11/1999 | Chin |
| 5,980,549 A | 11/1999 | Chin |
| 6,007,510 A | 12/1999 | Nigam |
| 6,010,510 A | 1/2000 | Brown et al. |
| 6,024,448 A | 2/2000 | Wu et al. |
| 6,033,395 A | 3/2000 | Peyman |
| 6,036,714 A | 3/2000 | Chin |
| 6,050,999 A | 4/2000 | Paraschac et al. |
| 6,055,990 A | 5/2000 | Thompson |
| 6,066,170 A | 5/2000 | Lee |
| 6,068,642 A | 5/2000 | Johnson et al. |
| 6,079,826 A | 6/2000 | Appleton et al. |
| 6,083,231 A | 7/2000 | Van Noy et al. |
| 6,086,202 A | 7/2000 | Chateau et al. |
| 6,090,141 A | 7/2000 | Lindstrom |
| 6,102,946 A | 8/2000 | Nigam |
| 6,110,166 A | 8/2000 | Juhasz et al. |
| 6,120,148 A | 9/2000 | Fiala et al. |
| 6,125,294 A | 9/2000 | Scholl et al. |
| 6,129,733 A | 10/2000 | Brady et al. |
| 6,139,560 A | 10/2000 | Kremer |
| 6,142,969 A | 11/2000 | Nigam |
| 6,143,001 A | 11/2000 | Brown et al. |
| 6,159,241 A | 12/2000 | Lee et al. |
| 6,171,324 B1 | 1/2001 | Cote et al. |
| 6,175,754 B1 | 1/2001 | Scholl et al. |
| RE37,071 E | 2/2001 | Gabrielian et al. |
| 6,183,513 B1 | 2/2001 | Guenthner et al. |
| 6,197,019 B1 | 3/2001 | Peyman |
| 6,197,057 B1 | 3/2001 | Peyman et al. |
| 6,197,058 B1 | 3/2001 | Portney |
| 6,203,538 B1 | 3/2001 | Peyman |
| 6,203,549 B1 | 3/2001 | Waldock |
| 6,203,557 B1 | 3/2001 | Chin |
| 6,206,919 B1 | 3/2001 | Lee |
| 6,210,005 B1 | 4/2001 | Portney |
| 6,214,015 B1 | 4/2001 | Reich et al. |
| 6,214,044 B1 | 4/2001 | Silverstrini |
| 6,217,571 B1 | 4/2001 | Peyman |
| 6,221,067 B1 | 4/2001 | Peyman |
| 6,228,113 B1 | 5/2001 | Kaufman |
| 6,228,114 B1 | 5/2001 | Lee |
| 6,248,111 B1 | 6/2001 | Glick et al. |
| 6,250,757 B1 | 6/2001 | Roffman et al. |
| 6,251,114 B1 | 6/2001 | Farmer et al. |
| 6,264,648 B1 | 7/2001 | Peyman |
| 6,264,670 B1 | 7/2001 | Chin |
| 6,264,692 B1 | 7/2001 | Woffinden et al. |
| 6,267,768 B1 | 7/2001 | Deacon et al. |
| 6,271,281 B1 | 8/2001 | Liao et al. |
| 6,277,137 B1 | 8/2001 | Chin |
| 6,280,449 B1 | 8/2001 | Blake |
| 6,280,470 B1 | 8/2001 | Peyman |
| 6,283,595 B1 | 9/2001 | Breger |
| 6,302,877 B1 | 10/2001 | Ruiz |
| 6,325,509 B1 | 12/2001 | Hodur et al. |
| 6,325,792 B1 | 12/2001 | Swinger et al. |
| 6,350,272 B1 | 2/2002 | Kawesch |
| 6,361,560 B1 | 3/2002 | Nigam |
| 6,364,483 B1 | 4/2002 | Grossinger et al. |
| 6,371,960 B2 | 4/2002 | Heyman et al. |
| 6,391,230 B1 | 5/2002 | Sarbadhikari |
| 6,398,277 B1 | 6/2002 | McDonald |
| 6,398,789 B1 | 6/2002 | Capetan |
| 6,428,572 B2 | 8/2002 | Nagai |
| 6,435,681 B2 | 8/2002 | Portney |
| 6,436,092 B1 | 8/2002 | Peyman |
| 6,447,519 B1 | 9/2002 | Brady et al. |
| 6,447,520 B1 | 9/2002 | Ott et al. |
| 6,458,141 B1 | 10/2002 | Peyman |
| 6,461,384 B1 | 10/2002 | Hoffmann et al. |
| 6,471,708 B2 | 10/2002 | Green |
| 6,474,814 B1 | 11/2002 | Griffin |
| 6,506,200 B1 | 1/2003 | Chin |
| 6,511,178 B1 | 1/2003 | Roffman et al. |
| 6,527,389 B2 | 3/2003 | Portney |
| 6,537,283 B2 | 3/2003 | Van Noy |
| 6,543,610 B1 | 4/2003 | Nigam |
| 6,544,286 B1 | 4/2003 | Perez |
| 6,551,307 B2 | 4/2003 | Peyman |
| 6,554,424 B1 | 4/2003 | Miller et al. |
| 6,554,425 B1 | 4/2003 | Roffman et al. |
| 6,557,998 B2 | 5/2003 | Portney |
| 6,581,993 B2 | 6/2003 | Nigam |
| 6,582,076 B1 | 6/2003 | Roffman et al. |
| 6,589,057 B1 | 7/2003 | Keenan et al. |
| 6,589,203 B1 | 7/2003 | Mitrev |
| 6,589,280 B1 | 7/2003 | Koziol |
| 6,592,591 B2 | 7/2003 | Polla et al. |
| 6,596,000 B2 | 7/2003 | Chan et al. |
| 6,605,093 B1 | 8/2003 | Blake |
| 6,607,537 B1 | 8/2003 | Binder |
| 6,607,556 B1 | 8/2003 | Nigam |
| 6,623,522 B2 | 9/2003 | Nigam |
| 6,626,941 B2 | 9/2003 | Nigam |
| 6,629,979 B1 | 10/2003 | Feingold et al. |
| 6,632,244 B1 | 10/2003 | Nigam |
| 6,641,577 B2 | 11/2003 | Bille |
| 6,645,246 B1 | 11/2003 | Weinschenk, III et al. |
| 6,648,877 B1 | 11/2003 | Juhasz et al. |
| 6,657,029 B2 | 12/2003 | Vanderbilt |
| 6,666,887 B1 | 12/2003 | Callahan et al. |
| 6,673,112 B2 | 1/2004 | Nigam |
| 6,702,807 B2 | 3/2004 | Peyman |
| 6,709,103 B1 | 3/2004 | Roffman et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,733,526 B2 | 5/2004 | Paul et al. |
| 6,808,262 B2 | 10/2004 | Chapoy et al. |
| 6,824,178 B2 | 11/2004 | Nigam |

(56) References Cited

U.S. PATENT DOCUMENTS

| | | |
|---|---|---|
| 6,849,090 B2 | 2/2005 | Nigam |
| 6,855,163 B2 | 2/2005 | Peyman |
| 6,875,232 B2 | 4/2005 | Nigam |
| 6,879,402 B2 | 4/2005 | Küchel |
| 6,881,197 B1 | 4/2005 | Nigam |
| 6,893,461 B2 | 5/2005 | Nigam |
| 6,949,093 B1 | 9/2005 | Peyman |
| 6,955,432 B2 | 10/2005 | Graham |
| 7,128,351 B2 | 10/2006 | Nigam |
| 7,585,075 B2 | 9/2009 | Marmo |
| 7,699,837 B2 | 4/2010 | Cox et al. |
| 7,776,086 B2 | 8/2010 | Miller |
| 7,976,577 B2 | 7/2011 | Silvestrini |
| 7,992,906 B2 | 8/2011 | Nigam |
| 8,057,541 B2 | 11/2011 | Dishler et al. |
| 8,162,953 B2 | 4/2012 | Dishler et al. |
| 8,685,292 B2 | 4/2014 | Mandler et al. |
| 2001/0027314 A1 | 10/2001 | Peyman |
| 2001/0051826 A1 | 12/2001 | Bogaert et al. |
| 2002/0010510 A1 | 1/2002 | Silvestrini |
| 2002/0055753 A1 | 5/2002 | Silvestrini |
| 2002/0101563 A1 | 8/2002 | Miyamura et al. |
| 2002/0103538 A1 | 8/2002 | Hughes et al. |
| 2002/0138069 A1 | 9/2002 | Peyman |
| 2003/0014042 A1 | 1/2003 | Juhasz et al. |
| 2003/0033010 A1 | 2/2003 | Hicks et al. |
| 2003/0069637 A1 | 4/2003 | Lynch et al. |
| 2003/0078487 A1 | 4/2003 | Jeffries et al. |
| 2003/0176855 A1 | 9/2003 | Gross et al. |
| 2003/0208190 A1 | 11/2003 | Roberts et al. |
| 2003/0220653 A1 | 11/2003 | Perez |
| 2003/0229303 A1 | 12/2003 | Haffner et al. |
| 2004/0019379 A1 | 1/2004 | Glick et al. |
| 2004/0034413 A1 | 2/2004 | Christensen |
| 2004/0054408 A1 | 3/2004 | Glick et al. |
| 2004/0073303 A1 | 4/2004 | Schanzlin |
| 2005/0080484 A1 | 4/2005 | Marmo et al. |
| 2005/0080485 A1 | 4/2005 | Nigam |
| 2005/0113844 A1 | 5/2005 | Nigam |
| 2005/0119738 A1 | 6/2005 | Nigam |
| 2005/0143717 A1 | 6/2005 | Peyman |
| 2005/0178394 A1 | 8/2005 | Slade |
| 2005/0182350 A1 | 8/2005 | Nigam |
| 2005/0182488 A1 | 8/2005 | Peyman |
| 2005/0203494 A1 | 9/2005 | Holliday |
| 2005/0222679 A1 | 10/2005 | Peyman |
| 2005/0246016 A1 | 11/2005 | Miller et al. |
| 2006/0004381 A1 | 1/2006 | Feingold et al. |
| 2006/0020267 A1 | 1/2006 | Marmo |
| 2006/0105309 A1 | 5/2006 | Stoll et al. |
| 2006/0116762 A1 | 6/2006 | Hong et al. |
| 2006/0134170 A1 | 6/2006 | Griffith et al. |
| 2006/0142780 A1 | 6/2006 | Pynson et al. |
| 2006/0142781 A1 | 6/2006 | Pynson et al. |
| 2006/0173539 A1 | 8/2006 | Shiuey |
| 2006/0235430 A1 | 10/2006 | Le et al. |
| 2007/0027538 A1 | 2/2007 | Aharoni et al. |
| 2007/0106318 A1 | 5/2007 | McDonald |
| 2007/0106376 A1 | 5/2007 | Roberts et al. |
| 2007/0129797 A1 | 6/2007 | Lang et al. |
| 2007/0182920 A1 | 8/2007 | Back et al. |
| 2007/0244559 A1 | 10/2007 | Shiuey |
| 2007/0255401 A1 | 11/2007 | Lang |
| 2007/0280994 A1 | 12/2007 | Cunanan |
| 2008/0243138 A1* | 10/2008 | Dishler .................. A61F 2/148 606/107 |
| 2008/0262610 A1 | 10/2008 | Lang et al. |
| 2008/0269771 A1 | 10/2008 | Fulcher |
| 2008/0275433 A1 | 11/2008 | Russmann et al. |
| 2008/0281304 A1 | 11/2008 | Campbell |
| 2009/0079940 A1 | 3/2009 | Dai et al. |
| 2009/0198325 A1 | 8/2009 | Holliday et al. |
| 2009/0216217 A1 | 8/2009 | Odrich et al. |
| 2009/0326650 A1 | 12/2009 | Zickler et al. |
| 2010/0210996 A1 | 8/2010 | Peyman |
| 2010/0241060 A1 | 9/2010 | Roizman et al. |
| 2010/0331831 A1 | 12/2010 | Bischoff et al. |
| 2011/0029073 A1 | 2/2011 | Liang |
| 2011/0149241 A1 | 6/2011 | Dai |
| 2011/0208300 A1 | 8/2011 | de Juan et al. |
| 2011/0218623 A1 | 9/2011 | Dishler et al. |
| 2011/0256806 A1 | 10/2011 | Monnoyeur |
| 2011/0290681 A1 | 12/2011 | Nigam |
| 2011/0319876 A1 | 12/2011 | Feingold |
| 2012/0046680 A1 | 2/2012 | Dishler et al. |
| 2012/0165823 A1 | 6/2012 | Dishler et al. |
| 2012/0203238 A1 | 8/2012 | Nigam |
| 2012/0231416 A1 | 9/2012 | Drapeau et al. |
| 2012/0238806 A1 | 9/2012 | Mangiardi et al. |
| 2012/0245592 A1 | 9/2012 | Berner et al. |
| 2013/0060255 A1 | 3/2013 | Feingold et al. |
| 2013/0123916 A1 | 5/2013 | Nigam et al. |
| 2013/0211523 A1 | 8/2013 | Southard et al. |
| 2013/0253529 A1 | 9/2013 | Walter et al. |
| 2013/0281993 A1 | 10/2013 | Dishler et al. |
| 2013/0317605 A1 | 11/2013 | Ide et al. |
| 2013/0324983 A1 | 12/2013 | Liang |
| 2013/0331935 A1 | 12/2013 | Krause et al. |
| 2014/0257477 A1 | 9/2014 | Plambeck et al. |
| 2014/0288540 A1 | 9/2014 | Bischoff et al. |
| 2015/0080865 A1 | 3/2015 | Holliday et al. |
| 2015/0297340 A1 | 10/2015 | Esguerra et al. |
| 2016/0184085 A1 | 6/2016 | Schneider et al. |

FOREIGN PATENT DOCUMENTS

| | | |
|---|---|---|
| EP | 0308077 A2 | 3/1989 |
| EP | 0420549 A2 | 4/1991 |
| EP | 0729323 B1 | 7/1998 |
| EP | 0668061 B1 | 9/2000 |
| JP | S5973622 A | 4/1984 |
| JP | 01-195853 | 8/1989 |
| JP | 02-211119 | 8/1990 |
| JP | 5502811 | 5/1993 |
| JP | H06510687 | 12/1994 |
| JP | 08-501009 | 2/1996 |
| JP | 9-504706 | 5/1997 |
| JP | 2000506056 | 5/2000 |
| JP | 2002537895 | 11/2002 |
| JP | 03-508135 | 3/2003 |
| JP | 2007500070 | 1/2007 |
| KR | 2001-0013218 | 2/2001 |
| WO | WO92/08423 A1 | 5/1992 |
| WO | WO93/05731 A1 | 4/1993 |
| WO | WO 96/26690 A1 | 9/1996 |
| WO | WO 98/08549 A1 | 3/1998 |
| WO | WO 98/48715 A1 | 11/1998 |
| WO | WO 99/17691 A1 | 4/1999 |
| WO | WO 99/21513 A1 | 5/1999 |
| WO | WO 99/30645 A2 | 6/1999 |
| WO | WO 00/38594 A1 | 7/2000 |
| WO | WO 03/041616 A1 | 5/2003 |
| WO | WO 03/061518 A2 | 7/2003 |
| WO | WO 03/101341 A2 | 12/2003 |
| WO | WO 2005/020792 A2 | 3/2005 |
| WO | WO 2005/107648 A2 | 11/2005 |
| WO | WO 2006/029316 A1 | 4/2006 |
| WO | WO 2006/060363 A2 | 6/2006 |
| WO | WO 2007/101016 A2 | 9/2007 |
| WO | WO 2007/132332 A2 | 11/2007 |
| WO | WO2010/084595 A1 | 7/2010 |

OTHER PUBLICATIONS

Nigam et al.; U.S. Appl. No. 14/160,438 entitled "Coreal Implant Applicators," filed Jan. 21, 2014.

Sharma et al.; U.S. Appl. No. 14/211,714 entitled "Pre-treatment haze reduction for corneal inlays,", filed Mar. 14, 2014.

Long et al.; U.S. Appl. No. 14/217,056 entitled "Anterior corneal shapes and methods of providing the shapes,", filed Mar. 17, 2014.

Patel et al.; Refractive index of human corneal epithelium and stroma; J. Refract. Surg.; 11(2); Abstract; Mar. 1995 (pubmed Abstract only).

(56) References Cited

OTHER PUBLICATIONS

Esguerra et al.; U.S. Appl. No. 14/463,355 entitled "Corneal implant storage, packaging, and delivery devices,", filed Aug. 19, 2014.
Alio, J. J., et al., "Intracorneal Inlay Complicated by Intrastomal Epithelial Opacification," Arch Ophthalmol, Oct. 2004; vol. 122; 6 pages.
Cheng, et al.; "Predicting subjective judgment of best focus with objective image quality metrics"; Journal of Vision; Apr. 23, 2004; vol. 4(4); pp. 310-321.
Churms, P.W., "The Theory and Computation of Optical Modifications to the Cornea in Refractive Keratoplasty," American Journal of Optometry & Physiological Optics, 56:2, pp. 67-74, Feb. 1979.
Huang et al.; Mathematical Model of Corneal Surface Smoothing After Laser Refractive Surgery; American Journal of Ophthalmology; Mar. 2003; pp. 267-278.
Lang, A.J. et al., "First order design of intracorneal inlays: dependence on keratometric flap and corneal properties," ARVO Abstracts 2006, poster No. 3591, May 3, 2006.
Liou, H. L. et al., "Anatomically accurate, finite model eye for optical modeling", Journal of the Optical Society of America, vol. 14, No. 8, Aug. 1997.
Marsack, et al.; "Metrics of optical quality derived from wave aberrations predict visual performance"; Journal of Vision; Apr. 23, 2004; vol. 4(4); pp. 322-328.
Navarro et al.; Accommodation-dependent model of the human eye with aspherics; J. Opt. Soc Am. A; vol. 2; No. 8; Aug. 1985; pp. 1273-1281.
Watsky, M.A. et al., "Predicting Refractive Alterations with Hydrogel Keratophakia," Investigative Opthalmology & Visual Science, vol. 26, pp. 240-243, Feb. 1985.
Schneider et al.; U.S. Appl. No. 13/549,007 entitled "Corneal Implant Retaining Devices and Methods of Use,", filed Jul. 13, 2012.
Schneider et al.; U.S. Appl. No. 13/619,955 entitled "Corneal Implant Inserters and Methods of Use,", filed Sep. 14, 2012.
Collins et al.; U.S. Appl. No. 14/575,833 entitled "Integrated part fixturing for lathing processes,", filed Dec. 18, 2014.
Sharma; U.S. Appl. No. 14/427,510 entitled "Corneal implant edges and methods of use,", filed Mar. 11, 2015.
Holliday et al.; U.S. Appl. No. 14/656,621 entitled "Methods of correcting vision,", filed Mar. 12, 2015.
Dymax; UV curable optical assembly; 2 pages; retrieved Mar. 4, 2015 from the internet (http:www.dymax.com/index.php/adhesives/optical).
Jankov et al.; Laser intrastromal keratoplasty—case report; J. Refract.Surg.; 20(1); pp. 79-84; Jan.-Feb. 2004.
Winn et al.; Factors affecting light-adapted pupil size in normal human subjects; Investigative Ophthalmology and Visual Science; 35(3); pp. 1132-1137; Mar. 1994.
Plambeck et al.; U.S. Appl. No. 15/163,610 entitled "Corneal implant storage and delivery devices,", filed May 24, 2016.

* cited by examiner

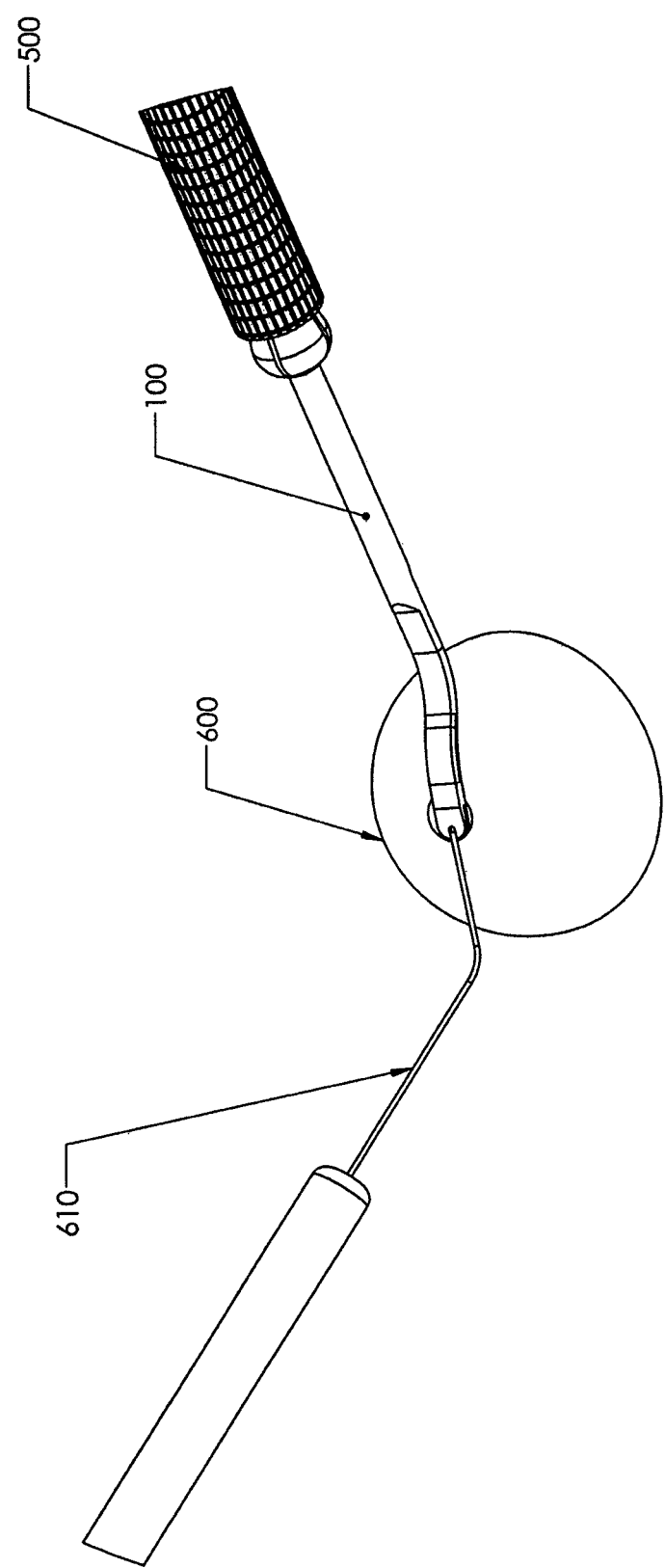

SECTION A-A

SECTION B-B
SCALE 6:1

CORNEAL IMPLANT INSERTERS AND METHODS OF USE

CROSS REFERENCE TO RELATED APPLICATIONS

This application is a continuation-in-part application of U.S. application Ser. No. 13/411,425, filed Mar. 2, 2012, now U.S. Pat. No. 8,540,727, which is a continuation application of U.S. application Ser. No. 11/692,835, filed Mar. 28, 2007, now U.S. Pat. No. 8,162,953. This application also claims priority to U.S. Prov. App. No. 61/535,744, filed Sep. 16, 2011. This application incorporates by reference herein all of the aforementioned applications.

This application is related to and incorporates by reference herein the disclosure of U.S. application Ser. No. 13/549,007, filed Jul. 13, 2012, the disclosure of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Corneal implants can correct vision impairment by positioning them on corneal tissue by creating a change in curvature of the anterior surface of a cornea and/or creating multifocalities within the cornea due to intrinsic properties of the implant. Corneal implants include onlays and inlays, but as used herein can also refer to contact lenses, or even to corneal replacement devices. An onlay is an implant that is placed over the stromal part of the cornea such that the outer layer of the cornea, i.e., the epithelium, can grow over and encompass the implant. An inlay is an implant that is implanted within corneal tissue beneath a portion of the corneal tissue by, for example, cutting a flap in the cornea and inserting the inlay beneath the flap. Both inlays and onlays can alter the refractive power of the cornea by changing the shape of the anterior cornea, by having a different index of refraction than the cornea, or both.

There is a need for improved apparatuses, systems and methods for inserting a corneal implant onto corneal tissue, including inserting it within a pocket created in the corneal tissue.

SUMMARY OF THE DISCLOSURE

One aspect of the disclosure is a corneal implant inserter apparatus, comprising: a holding space at a distal end of an elongate body, wherein the holding space is adapted to house a corneal implant therein in a substantially unstressed configuration; a fluid disposed in the holding space such that the corneal implant is retained within the holding space due to the surface tension of the fluid; and a channel extending within the elongate body such that the channel is in fluid communication with the holding space.

In some embodiments the channel has a maximum width that is less than a maximum width of the holding space. The channel maximum width can be less than half of the maximum width of the holding space.

In some embodiments the holding space has a generally flat top and a generally flat bottom. The corneal implant can be a corneal inlay with an anterior surface that is substantially parallel to the generally flat top and a posterior surface that is substantially parallel to the generally flat bottom.

In some embodiments the channel extends from the holding space to a proximal end of the elongate body.

In some embodiments the holding space and the channel are together adapted to hold between about 0.5 and about 4.0 microliters therein.

One aspect of the disclosure is a corneal implant inserter apparatus, comprising: a holding space at a distal end of an elongate body, wherein the holding space is adapted to house a corneal implant therein; a channel with a maximum width less than a maximum width of the holding space, wherein the channel is in fluid communication with the holding space and extends from the holding space within the elongate body.

In some embodiments the channel maximum width is less than half of the holding space maximum width.

In some embodiments the channel extends from the holding space to a proximal end of the elongate body.

In some embodiments the corneal implant is retained within the holding space in a substantially unstressed configuration. The holding space can have a generally flat top and a generally flat bottom, and wherein the corneal implant can be a corneal inlay with an anterior surface that is substantially parallel to the generally flat top and a posterior surface that is substantially parallel to the generally flat bottom.

In some embodiment the apparatus further comprises a fluid disposed in the holding space such that the corneal implant is retained within the holding space due to the surface tension of the fluid.

In some embodiment the holding space has a generally flat top and a generally flat bottom.

In some embodiments the holding space and the channel are together adapted to hold between about 0.5 and about 4.0 microliters therein.

One aspect of the disclosure is a corneal implant inserter apparatus, comprising: an elongate body comprising a distal holding space in fluid communication with a channel extending through the elongate body, wherein the holding space has a generally flat top and a generally flat bottom; and a corneal implant retained in the holding space between the generally flat top and the generally flat bottom.

In some embodiments the apparatus further comprises a fluid disposed in the holding space such that the corneal implant is retained within the holding space due to the surface tension of the fluid. The corneal implant can be retained in the holding space in a substantially unstressed configuration. The corneal implant can have an anterior surface that is substantially parallel to the generally flat top and a posterior surface that is substantially parallel to the generally flat bottom.

In some embodiments the channel has a maximum width that is less than a maximum width of the holding space.

In some embodiments the channel extends from the holding space to a proximal end of the elongate body.

In some embodiments the holding space and the channel are together adapted to hold between about 0.5 and about 4.0 microliters therein.

One aspect of the disclosure is a corneal implant inserter system, comprising: a corneal implant inserter comprising a channel fluidly connecting a holding space in a distal portion of the inserter and a proximal end of the corneal implant inserter; a fluid disposed in the holding space such that a corneal implant is retained in the holding space due to the surface tension of the fluid; and a fluid delivery device adapted to be positioned relative to the corneal implant inserter such that it is in fluid communication with the corneal implant inserter channel such that fluid can be delivered from the fluid delivery device into the channel to deploy the corneal implant from the holding space.

In some embodiments the system further comprises a hub that is adapted to receive a proximal end of the corneal implant inserter therein, and wherein the hub is adapted to engage the fluid delivery device such that the fluid delivery device, the hub, the channel, and the holding space are in fluid communication.

One aspect of the disclosure a method of deploying a corneal implant onto corneal tissue, comprising: providing a corneal implant inserter with a corneal implant retained in a holding space in a substantially unstressed configuration in a distal region of the inserter; and delivering fluid from a delivery device into a channel extending through the corneal implant inserter, wherein the channel is in fluid communication with the holding space, and wherein delivering the fluid deploys the corneal implant from the holding space and onto corneal tissue.

In some embodiments the method further comprises creating a corneal flap and lifting the flap to expose the corneal tissue prior to the delivering step.

In some embodiments the method further comprises applying a force on the corneal implant with a tool to assist in deploying the corneal implant from the holding space.

In some embodiments applying a force on the implant with a second tool comprises positioning the tool in a slot formed in a top portion of the holding space.

In some embodiments the method further comprises, prior to the delivering step: creating a corneal pocket within the cornea; creating an access channel to the pocket; and advancing the holding space into the access channel and towards the pocket.

In some embodiments the method further comprises: creating a second access channel to the pocket; positioning a tool in the second access channel; and applying a force on the corneal implant with the tool to assist in deploying the corneal implant from the holding space.

DETAILED DESCRIPTION

Figure 1:
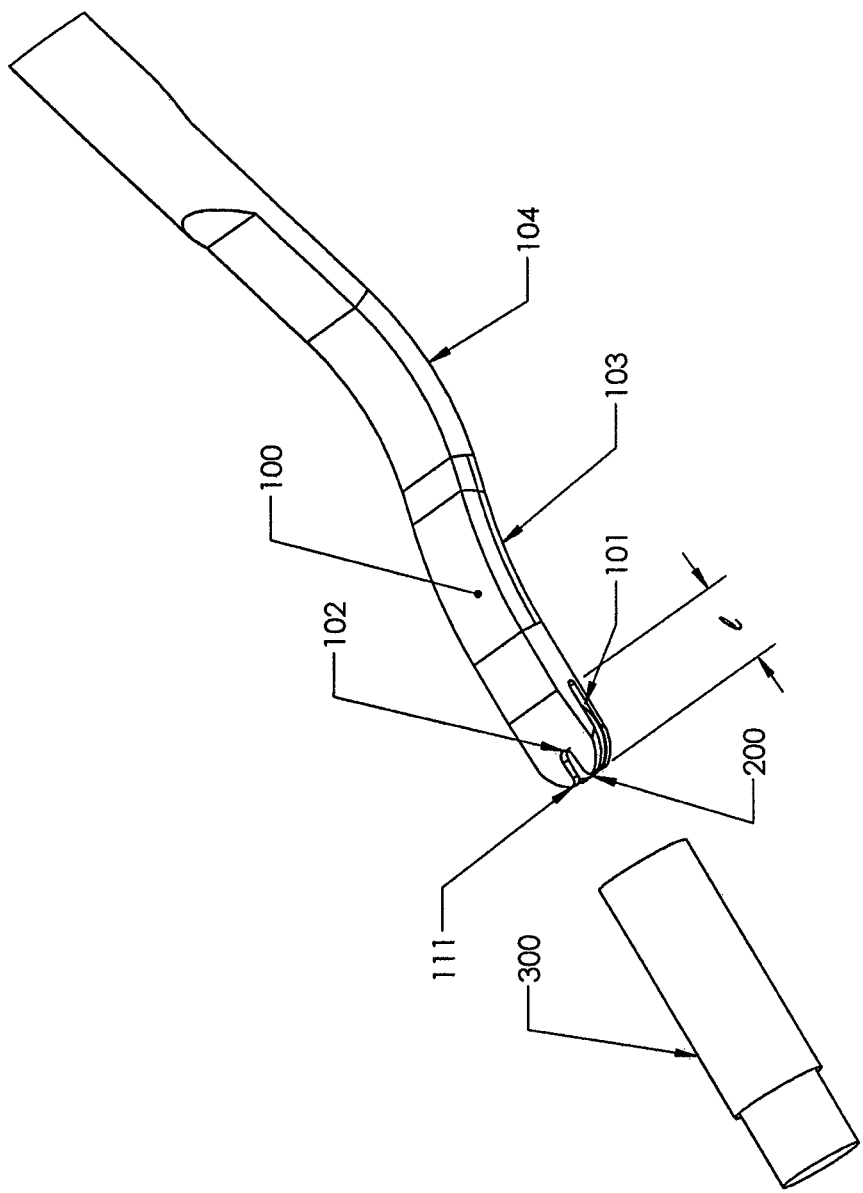
FIGS. 1-5D illustrate an exemplary corneal implant insertion system.

The disclosure herein generally describes devices that are adapted to insert corneal implants onto corneal tissue, and their methods of use. The methods of use include inserting the corneal implants into a pocket created in the cornea. The methods of use also include inserting the corneal implants onto corneal tissue after a flap has been created in the cornea. Some devices are adapted to deliver fluid to an implant holding space to at least assist in the deployment of the implant from the holding space and onto corneal tissue.

FIGS. 1-5 show an exemplary corneal implant insertion system. The disclosure herein focuses on devices that are adapted to deliver corneal inlays or onlays onto corneal tissue, but the devices herein can also be used to deliver other suitable ocular devices, such as contact lenses. The exemplary insertion system is also adapted for storing the corneal implant. The exemplary insertion system includes inserter 100 having an elongated body, which can be made of titanium, stainless steel, plastic, or any other suitable material. Inserter 100 comprises a distal portion having generally flat top and bottom surfaces. The distal portion of inserter 100 includes clearance bend 104 to provide clearance between the inserter and a patient's facial features (e.g., nose, cheeks, etc.) as explained further below. The distal portion of inserter 100 also includes additional curved portion 103 that is contoured to generally follow the shape of a patient's cornea as explained further below. Curved portion 103 is concave on the bottom.

The distal portion of inserter 100 further includes holding space 101 that is adapted to receive corneal implant 200 therein. Saline, BSS, or any other suitable solution (not shown in FIGS. 1-5) is positioned in holding space 101 with corneal implant 200, and the corneal implant 200 is maintained in holding space 101 due to the surface tension of the fluid. The fluid stays in holding space 101 due to capillary forces, which keeps the implant hydrated. The inserter also includes top and bottom inserter slots 102 and 110 on the top and bottom surfaces of the distal portion, as is shown in FIG. 4. As explained below, inserter slots 102 and 110 allow a physician or other user to view the patient's cornea through the slots for precise placement of implant 200. In addition, top inserter slot 102 allows the user to insert a device in top inserter slot 102 to apply a force onto implant 200 while it is in holding space 101. The user can then retract inserter 100 while applying the force on implant 200 to maintain the position of implant 200 relative to inserter 100, thereby removing implant 200 from holding space 101. The user may hold down implant 200 with a surgical tool, such as a cannula, Sinskey hook, or other tool that fits through top inserter slot 102. Top inserter slot 102 extends to leading edge 111 of inserter 100 so that the tool can hold down implant 200 as inserter 100 is retracted. Leading edge 111 of the inserter can be rounded (as shown) to prevent damage to the cornea.

As can be seen in FIG. 4, the width "w" dimension of holding space 101 is slightly greater than the diameter of corneal inlay 200 in a substantially unstressed configuration. In a merely exemplary embodiment, inlay 200 has a diameter of about 1.5 mm and the width "w" of holding space 101 is between about 1.6 and about 1.7 mm. The rounded leading edge 111 of inserter 100 is adapted to follow the general curvature of the perimeter of implant 200. The center length "l" (see FIGS. 1 and 3) of the holding space 101 is slightly larger than the diameter of the implant 200. As shown in FIGS. 1 and 3, the center length "l" extends from the center of leading edge 111 to back wall 113 of holding space 101. The geometry of holding space 101 and the surface tension of the saline in holding space 101 keeps implant 200 substantially centered in holding space 101. The height of the holding space 101 in which the implant is disposed can be several times larger than the thickness of implant 200 to ensure that a sufficient amount of fluid (e.g., saline) can be maintained in holding space 101 to keep the implant sufficiently hydrated.

Exemplary corneal inlays that can be positioned onto corneal tissue using the inserter devices and methods of use herein can be found described in U.S. Pat. No. 8,057,541, filed Oct. 30, 2006; U.S. Pub. No. 2008/0262610, filed Apr. 20, 2007; U.S. Pub. No. 2009/0198325, filed Apr. 3, 2009; U.S. Pub. No. 2011/0218623, filed Sep. 8, 2010, all of which are incorporated by reference herein.

In some embodiments inserter 100 is manufactured from a rod that is cut and bent to form the configuration of inserter 100 shown in FIG. 1. In one particular embodiment, a cylindrical titanium rod is cut and bent to form the inserter. In this particular embodiment, the proximal portion of the inserter is generally cylindrical, with angled transition portions that are tapered down to the distal portion of the inserter. Exemplary tapers can be seen in FIGS. 1 and 2.

Figure 2:
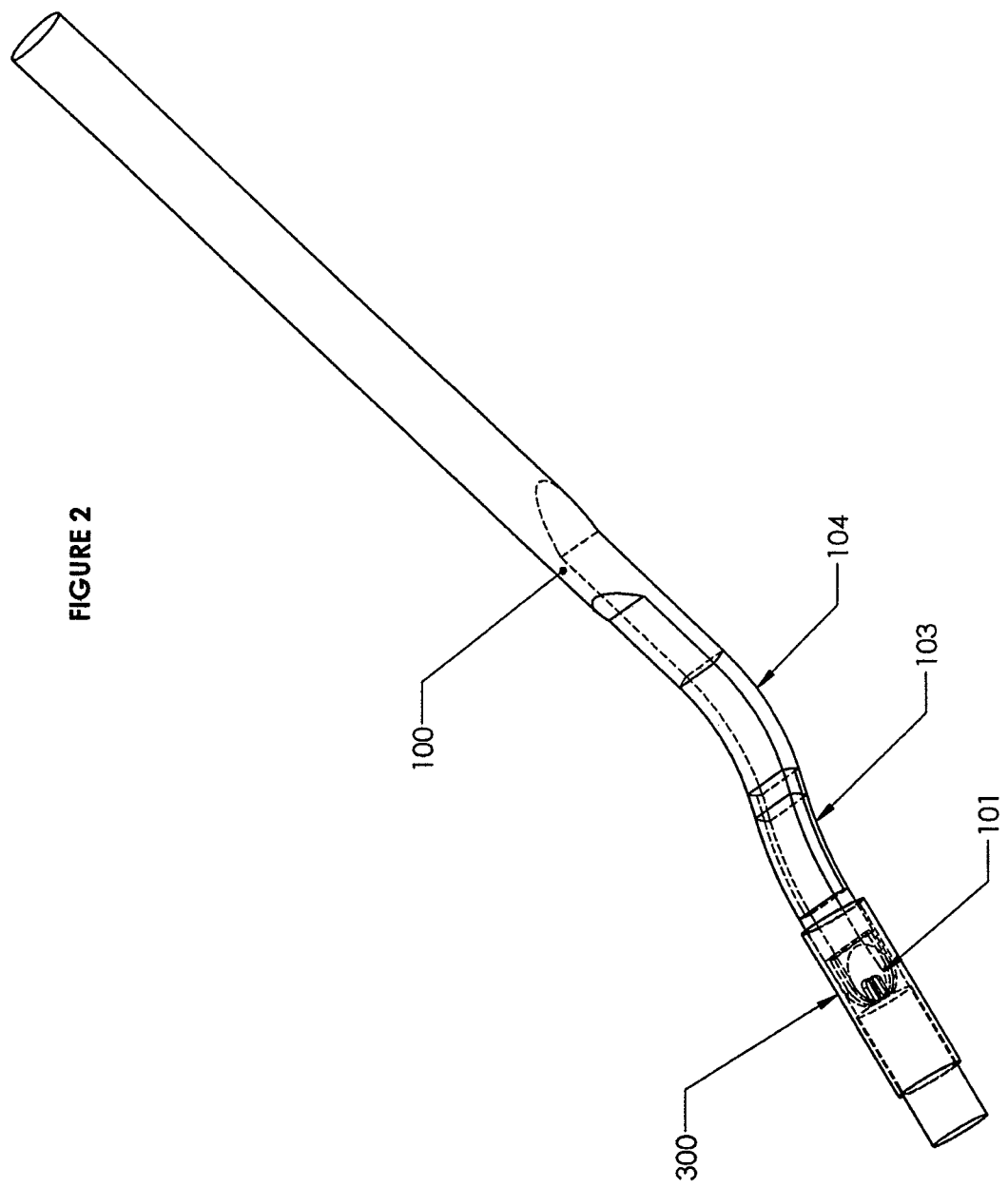
Figure 3:
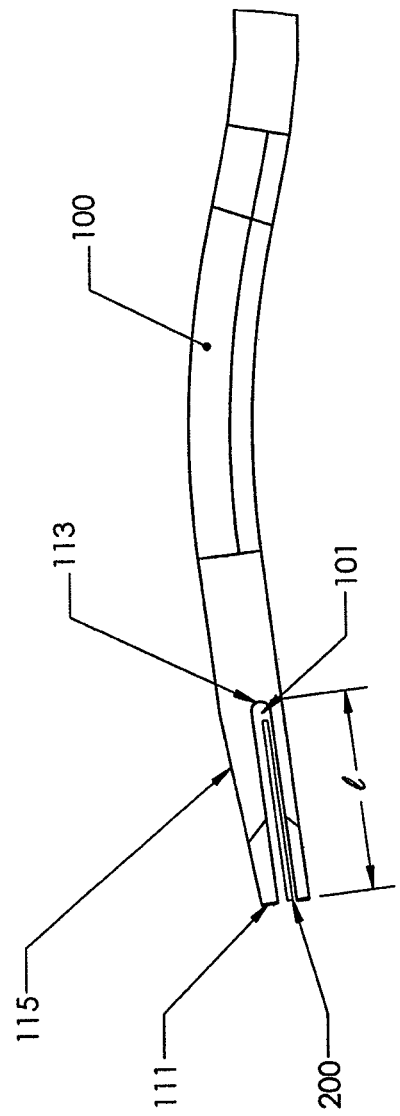
Figure 4:
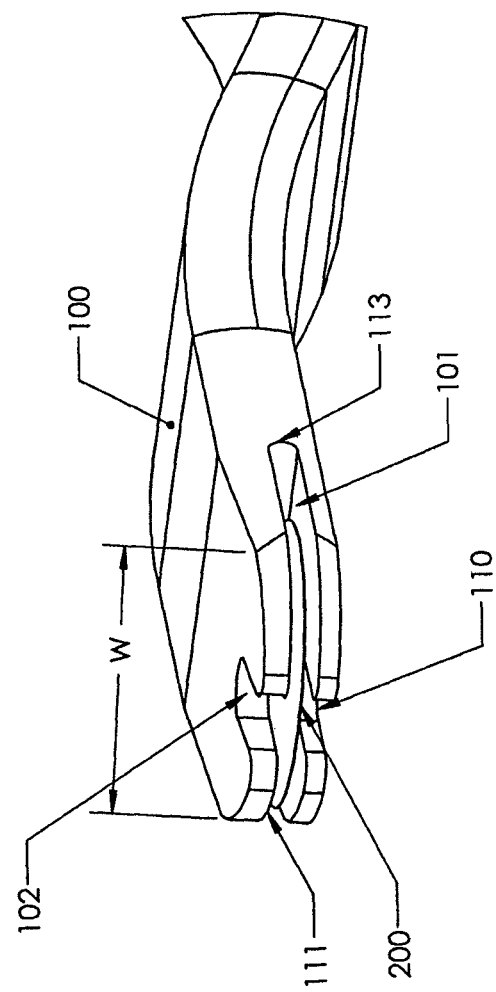

The exemplary inserter system in FIGS. 1-5 additionally includes inserter cap 300 shown in FIGS. 1 and 2. Cap 300 generally helps keep the implant within the holding space of the inserter. Cap 300 can be made of Teflon ("PTFE") or other suitable material. In some embodiments, inserter cap 300 is generally cylindrical and can be fitted snugly on the distal end of inserter 100 by engaging the sides of inserter 100 as shown in FIG. 2. Additional details of exemplary caps that can be used can be found in U.S. application Ser. No. 13/549,007, filed Jul. 13, 2012, the complete disclosure of which is incorporated by reference.

Figure 6:
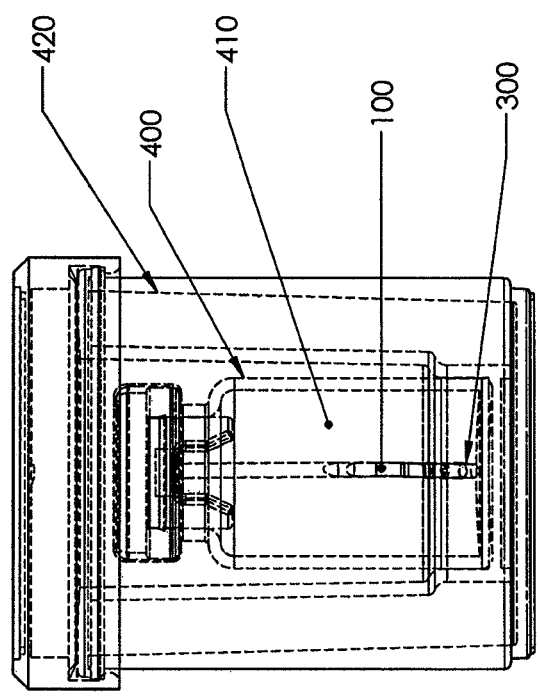
FIG. 6 illustrates an exemplary storage container with an insertion system therein.

In an exemplary method of use, the implant is preloaded into the holding space of the inserter and packaged for later use by the physician or other user during an implantation procedure. In this embodiment, the implant is preloaded into the holding space of the inserter with the top, or anterior, surface of the implant orientated to face the top surface of the inserter. The implant may be preloaded by submerging both the implant and the holding space of the inserter in a solution (e.g., saline) and inserting the implant into the holding space while they are both submerged. After the implant is preloaded in the inserter, the inserter cap is positioned on the distal end of the inserter. The cap may be placed on the inserter while the holding space is still submerged in the solution. The preloaded inserter assembled with the inserter cap is placed into vial 400 or other storage container filled with saline 410 or other suitable solution as shown in FIG. 6. The inserter cap prevents the implant from moving out of the inserter when placed in vial 400 filled with saline 410. Vial 400 is capped and placed in outer package 420, which is sterilized to store the insertion system until use.

An exemplary implantation procedure using the exemplary insertion system shown in FIGS. 1-6 and described above will now be described. In this embodiment, inserter 100 preloaded with a corneal implant is removed from outer package 420 and vial 400 that is filled with saline 410. The saline disposed within the space between cap 300 and inserter 101 is removed by placing a sponge (not shown) or other absorbent material on the open end on inserter cap 300. The sponge draws out the saline from the interior of cap 300 by capillary action through the opening between cap 300 and inserter 101. In embodiments in which cap 300 has a generally cylindrical shape, the opening is formed between the cylindrical cap 300 and the generally flat top and bottom surfaces of inserter 100. The saline is removed from the space between cap 300 and inserter 100 while cap 300 is still on inserter 100. This is done to prevent cap 300 from pulling implant 200 out of inserter 100 because of capillary action when cap 300 is removed from inserter 100. After the saline is removed, cap 300 is removed from inserter 100. At this point, a small amount of saline or BSS may be applied to holding space 101 of inserter 100 to keep implant 200 hydrated. The saline stays in holding space 101 due to capillary forces, thereby keeping implant 200 hydrated during the procedure. Further, the surface tension of the saline keeps implant 200 in holding space 101 of inserter 100 so that implant 200 does not fall out of inserter 100 during the procedure. This surface tension and the geometry of holding space 101 keep implant 200 substantially centered in inserter 100.

To enable a user to better hold inserter 100, handle 500 may be attached to the proximal end of inserter 100 as shown in FIG. 5A. The handle may be similar to handles that attach to disposable blades.

Additionally, the user may determine the proper orientation of the implant based on features of inserter 100. For example, when the top of inserter 100, and hence implant 200, are facing upward, the concave bottom surface of curved portion 103 is facing downward.

Figure 5B:
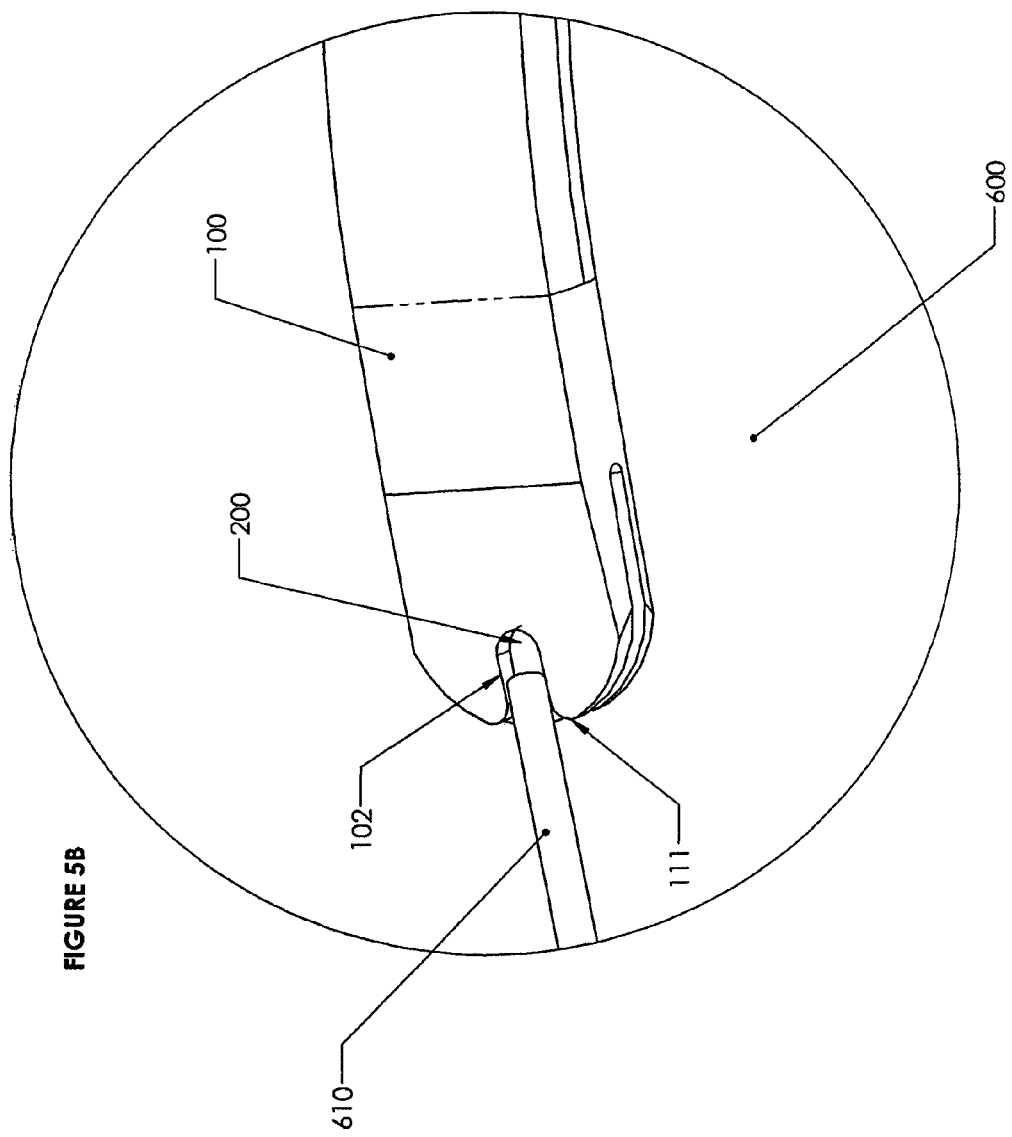
Figure 5C:
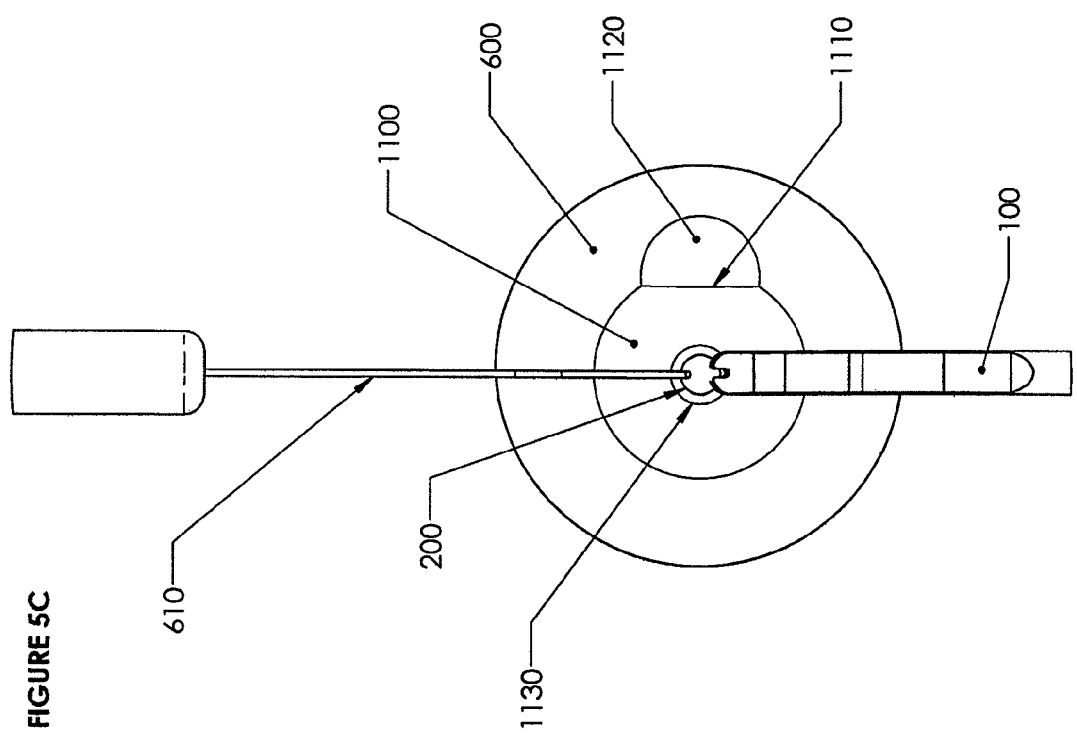

In embodiments in which an inlay is being implanted, after the cap has been removed, the user may then implant the corneal implant in or on the patient's cornea. In some embodiments the corneal implant is positioned under a flap created in the cornea. Techniques to create corneal flaps are known, such as by mechanical methods or using a laser. Once created, the flap is then lifted to expose the cornea's interior, e.g., stroma bed of the cornea. An example of this is shown in FIG. 5C, in which flap 1120 is cut into cornea 600 and pulled backed to expose stroma bed 1100 of the cornea. Flap 1120 is attached to the cornea 600 by flap hinge 1110. Flap 1120 can be made using a laser, e.g., femtosecond laser, a mechanical keratome or manually. Several methods for forming flaps in corneal tissue, and other related information, are described in further detail in co-pending U.S. patent application Ser. No. 10/924,152, filed Aug. 23, 2004, entitled "Method for Keratophakia Surgery," which is fully incorporated by reference herein. Once the interior cornea is exposed, the user positions inserter 100 so that implant 200 is at the desired location on the cornea 600, e.g., the patient's pupil or visual axis as shown in FIG. 5A. Prior to positioning inserter 100, the user may use a sponge or other absorbent material to remove excess fluid on the outer surface of inserter 100 being careful not to remove the saline from holding space 101. Clearance bend 104 allows the inserter to clear the patient's facial features (e.g., nose) as the surgeon manipulates inserter 100. When implant 200 is at the desired location, the user holds down the implant 200 on cornea 600 using a surgical cannula, Sinskey Hook or other tool 610 such that implant 200 gently touches the stroma bed of cornea 600 through bottom slot 110. Tool 610 holds down implant 200 through top inserter slot 102 as shown in FIG. 5B. The user then retracts inserter 100 from cornea 600 to release implant 200 from inserter 100 and deposit implant 200 at the desired location. If implant 200 is not precisely at the desired location, then the user can gently move implant 200 into position using a surgical sponge, rounded-tip tool, or other tool. In the example shown in FIG. 5C, implant 200 is centered on pupil 1130. After implant 200 is correctly positioned, the user places flap 1120 back over implant 200.

Implant 200 may be implanted concurrent with a LASIK procedure or post-LASIK. Since a flap is cut into the cornea during a LASIK procedure, the same flap may be used to implant the corneal implant. If the implant is implanted post-LASIK, then the LASIK flap may be re-opened or the inserter may be advanced between the flap and the underlying corneal tissue to the desired position. In this example, the LASIK procedure may be used to correct distance vision while the implant is used to provide near vision. Additional details can be found, for example, in U.S. patent application Ser. No. 11/554,544, entitled "Small Diameter Inlays," filed on Oct. 30, 2006, now U.S. Pat. No. 8,057,541, the specification of which is incorporated herein by reference.

The implants can be positioned under a newly created and opened flap, a previously created and re-opened flap, a newly created but unopened flap (e.g., a femtosecond laser makes a flap but it is not lifted and perhaps all of the corneal tags are not broken), a previously created and unopened flap, or an actual purpose-made pocket/channel.

In embodiments in which the implant is positioned under a flap that is not opened (whether newly created or previously created) the distal portion of the inserter may be inserted between the flap and the underlying corneal tissue and advanced between the flap and underlying corneal tissue to the desired position in the cornea. The distal portion of the inserter preferably has a thin cross-section so that the inserter does not induce corneal stretching. The curved portion of the inserter follows the curvature of the cornea allowing the inserter to more easily move between the flap and underlying corneal tissue while minimizing stress on the cornea. Further, the top surface of the inserter preferably has a downward sloping portion 115 that slopes downward to the leading edge of the inserter as shown in FIG. 3. In these embodiments, a surgical cannula or other tool may also be inserted between the flap and the underlying corneal tissue to hold down the implant at the desired location and release the implant from the inserter.

The devices and systems described herein can also be used in the delivery of corneal implants using different methods to access the interior of the cornea. For example, the interior of the cornea may be accessed through a lamellar pocket, channel, or pathway cut into the cornea. A "pocket" is generally referred to as a recess formed within the corneal tissue for receiving the corneal implant, and which may be accessed via a channel formed in the cornea. Methods of creating pockets are known, such as may be found described in United States Patent Application Publication No. 2003/0014042, published Jan. 16, 2003, entitled "Method of Creating Stromal Pockets for Corneal Implants," which is also fully incorporated by reference herein. Additional exemplary methods and devices for creating corneal pockets, or corneal channels, can be found in U.S. Pub. No. 2012/0046680, filed Aug. 23, 2010, the disclosure of which is fully incorporated by reference herein.

Figure 5D:
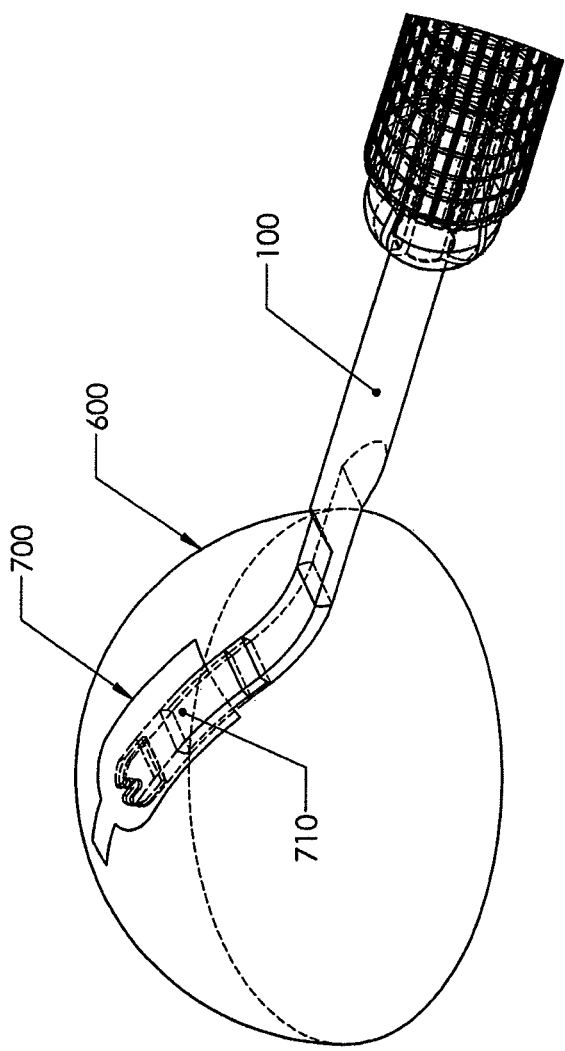

In an exemplary method of use, the inserter may be inserted into a channel or pocket cut into the cornea and advanced through the channel to position the implant at the desired location in the corneal pocket. A second channel may also be cut into the cornea to provide access for a surgical cannula or other tool used to hold down the implant at the desired location. FIG. 5D shows an example of inserter 100 placing implant (not shown) within pocket 700 formed in cornea 600 through an opening 710.

Figure 7A:
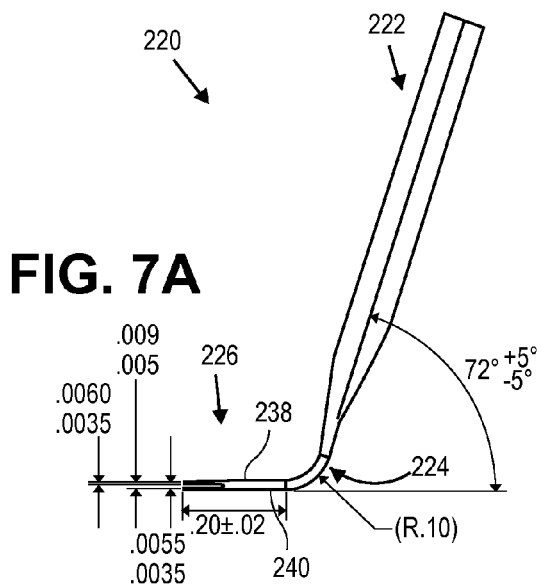
FIGS. 7A-7E illustrate an exemplary corneal implant insertion system.
Figure 7B:
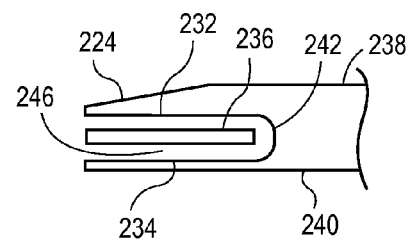
Figure 7C:
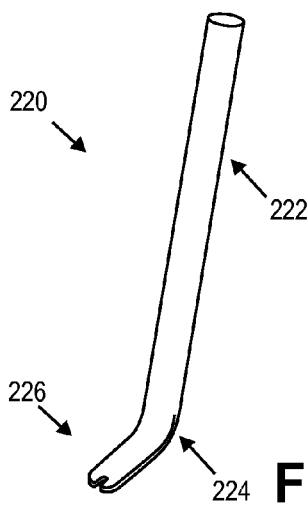
Figure 7D:
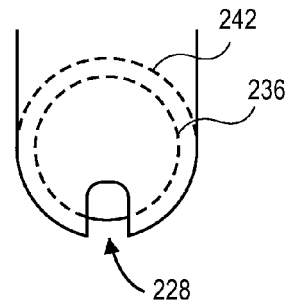

FIGS. 7A-7E illustrate an additionally exemplary embodiment of a corneal implant inserter, or delivery, device. Delivery device 220 includes distal portion 226, intermediate portion 224, and proximal portion 222. Distal portion 226 includes holding region 246 (see FIG. 7C), in which implant 236 is disposed. A fluid is disposed within holding region 246 such that implant 236 is retained within holding area 246 by capillary forces. Holding region 246 is defined by upper surface 232, lower surface 234, and proximal surface 242, as shown in FIGS. 7C (side view) and 7D (top view). Upper surface 232 and lower surface 234 are generally flat, while proximal surface 242 is curved and connects upper surface 232 and lower surface 234. While proximal surface 242 is shown in FIG. 7D as curved across the width of distal portion 226, proximal surface 242 could be substantially flat across the width of distal region 226.

Distal portion 226 has a generally flat configuration. Upper surface 238 is substantially flat, with surface 244 tapering slightly downward towards the distal end of distal portion 226. Bottom surface 240 is substantially flat and extends from the bend in intermediate region 224 to the distal end of distal portion 226.

In this embodiment holding area 246 and implant 236 are sized and shaped such that implant 236 is disposed within holding area 246 in a substantially non-deformed, or non-stressed, configuration. The substantially non-deformed configuration is substantially the same configuration that the implant is in after it is positioned in or on the subject's cornea. This can be beneficial since the implant might be retained in the holding space for an extended period of time, such as during shipping and storage prior to use. Keeping the implant in a substantially non-stressed, or non-deformed configuration, can reduce the likelihood of damage and increase the shelf-life of the implant. In some embodiments the implant is a corneal inlay that is adapted to be implanted within the cornea to treat presbyopia. The inlay has a diameter between about 1 mm about 3.5 mm. The relatively small diameter size allows for the width of the holding space to be relatively small and still be adapted to house the inlay therein in a non-deformed and substantially non-stressed configuration. The relatively small width of the inserter also reduces the likelihood of damage to corneal tissue when the inlay is positioned into a pocket via an access channel.

The dimensions and tolerances provided in FIGS. 7A-7E and throughout this disclosure are in inches and are merely illustrative and are not meant to be limiting. The dimensions of the inserters herein can be modified as desired.

Distal portion 226 also includes removal slot 228 that extends through the top and bottom surfaces of the distal portion. A removal tool can be positioned within the slot as described above to apply a gentle force to the implant while the inserter 220 is retracted, thereby removing the implant from the inserter and onto the corneal bed, as is described in more detail in U.S. Pat. No. 8,162,953, filed Mar. 28, 2007, the disclosure of which is incorporated by reference herein.

Device 220 shown in FIGS. 7A-7E can be used to deliver a corneal implant under a flap or within a pocket, both of which are described herein.

The inserter in FIGS. 7A-7E has a generally flat distal portion, while the inserter in the embodiment shown in FIG. 1 has a second bend 103. The flat bottom can improve the line of sight when positioning the inserter over the patient's pupil. Additionally, when used to deliver the implant, the inserter is intended to be angled approximately about 15 to about 20 degrees relative to the stroma bed. When a delivery device has a curved bottom, as opposed to a flat bottom, the user may have a natural tendency to place the device flat on the stroma bed such that the curve of the device matches the curve of stromal bed. In this situation the angle of the device relative to the stromal bed is substantially zero. Because this can be a suboptimal position for the inserter, a flat bottom can eliminate that tendency and provide a better positioning angle.

Figure 7E:
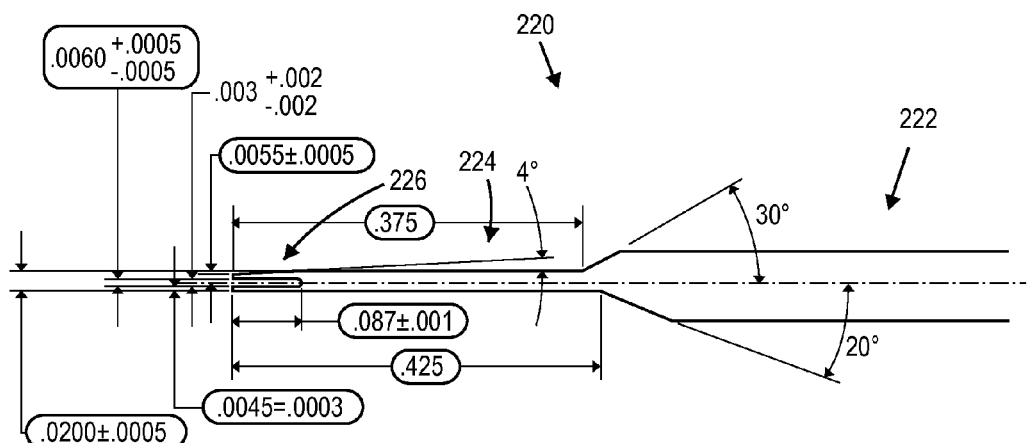

FIG. 7E illustrates device 220 prior to forming the bend in intermediate section 224 and includes additional exemplary dimensions. In some embodiments the device is formed of titanium, but any other suitable material can be used.

Figure 8A:
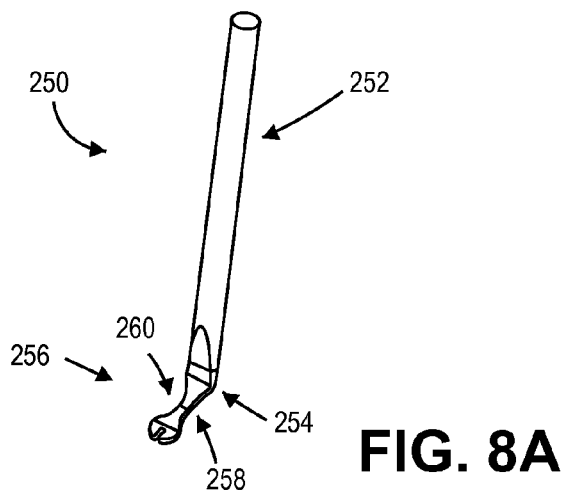
FIGS. 8A-8C illustrate an exemplary corneal implant insertion system.
Figure 8B:
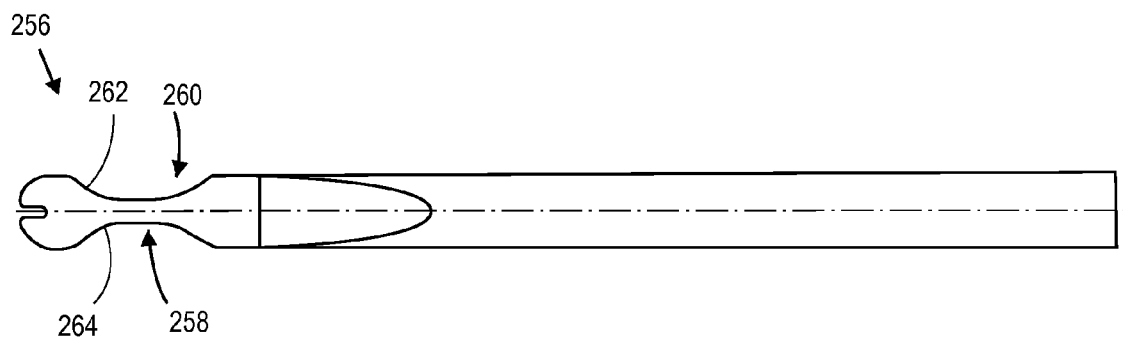
Figure 8C:
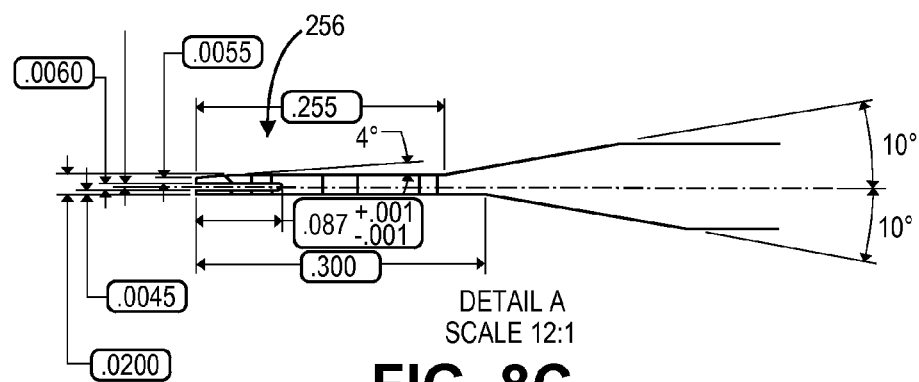

FIGS. 8A-8C illustrate an additional exemplary corneal implant delivery device 250. Device 250 includes a proximal section 252 and intermediate section 254 with a clearance bend, similar to the embodiment in FIGS. 7A-7E. Device 250 also includes a distal section 256, which has a general tear-drop configuration. Distal section 256 includes side surfaces 262 and 264, which taper towards the longitudinal axis of distal section 256, then extend parallel to it, before tapering outwards away from the longitudinal axis. The side surfaces form general indentations 258 and 260 in distal section 256.

Due to the indentations, device 250 has less material in the distal section 256 that the device in FIGS. 7A-7E. Less material provides better visualization of the eye, which in use is positioned below the inserter, relative to the user's field of view. The configuration of distal end 256 makes it easier for the user to position the delivery device in the correct position, which makes it easier to position the corneal implant in the correct position, such as when positioning a corneal inlay on the stromal bed within the pupil.

While device 250 has a tear-drop configuration, any distal portion configuration that does not have completely flat sides in a top view of the device can be used to help provide better visualization of the eye. Additionally, the device in FIGS. 8A-8C can optionally have a curved bottom surface as is shown in the embodiment in FIG. 1.

FIGS. 9-19D illustrate embodiments in which the inserter is adapted to allow for the delivery of fluid to the holding space to deploy, or at least assist in the deployment of, the corneal implant from the holding space and onto corneal tissue.

Figure 9:
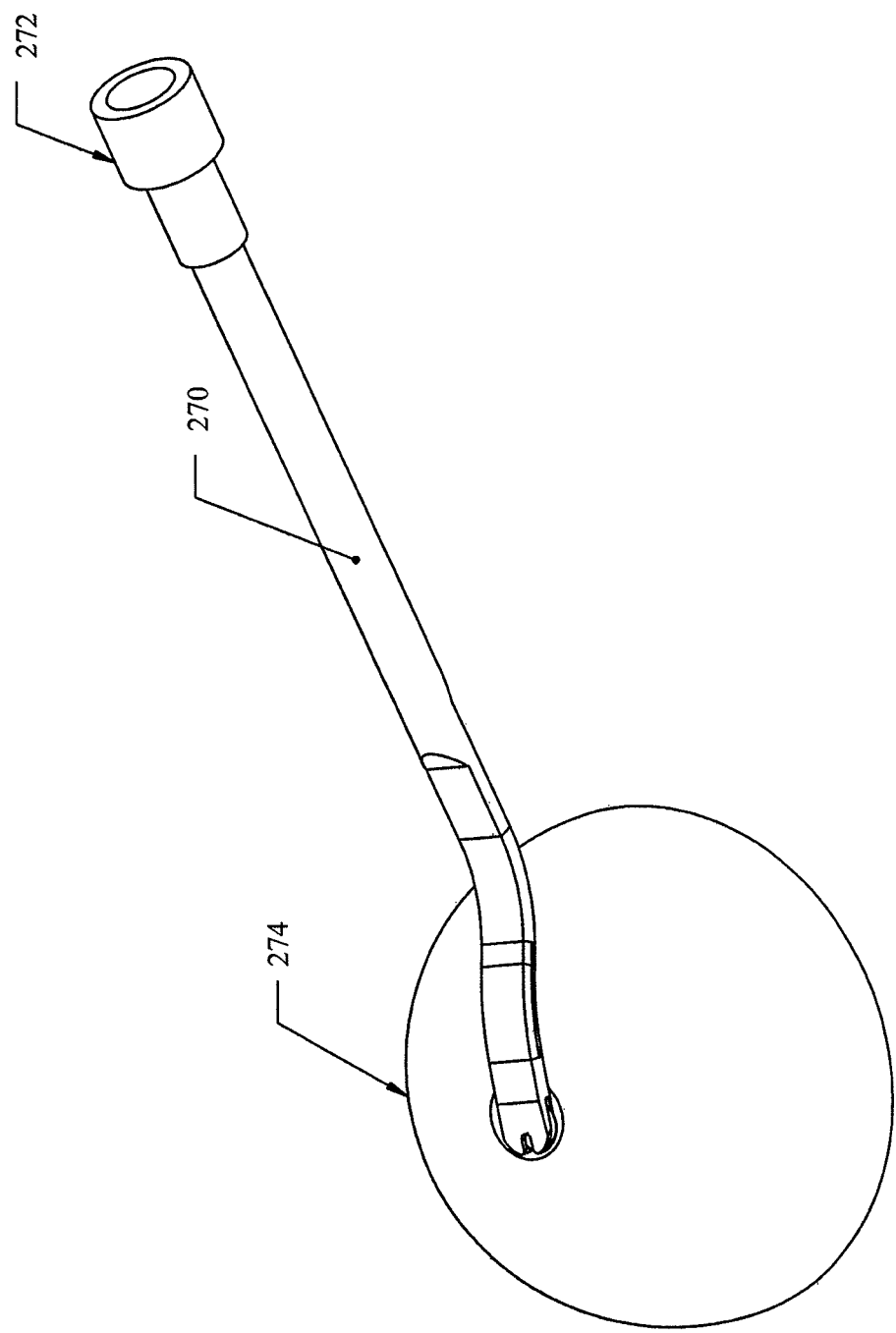
FIG. 9 illustrates an exemplary inserter that includes a channel extending from the proximal end of the inserter to the holding space.
Figure 10:
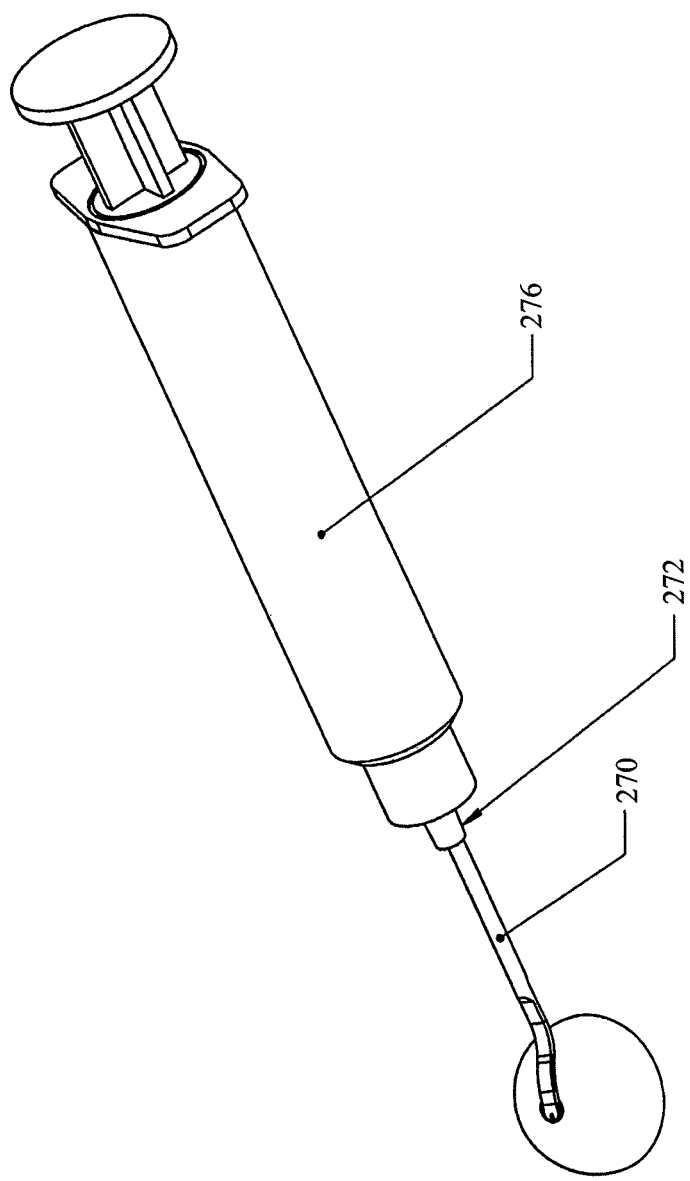
FIG. 10 illustrates a syringe connected to a proximal end of an inserter.

FIG. 9 illustrates inserter 270 that includes a channel extending from the proximal end of the inserter 270 to the holding space. The channel is in fluid communication with the holding space. The proximal end of inserter 270 can be connected to a syringe such that fluid can be delivered through the channel and into the holding space to gently push the implant out of the holding space and onto corneal tissue. The channel also allows fluid to be delivered via the channel to the holding space to hydrate the implant. For example, when the inserter is positioned such that the implant (which is still retained within the inserter) is at the desired location on the cornea, the user delivers fluid through the channel to help release the implant from the holding space. The fluid delivery to deploy the implant can be performed instead of, or in conjunction with, using a tool positioned in the top slot to hold down the implant while the inserter is retracted, as is described above. Thus, the implants can be deployed solely with fluid delivered through the channel, or with a combination of fluid delivery and mechanical forces with a second tool. FIG. 9 shows exemplary inserter 270 comprising luer lock 810 at the proximal end of inserter 270 that is configured to mate with a corresponding luer lock of a syringe or other fluid delivering device (not shown). Once the syringe is mated with inserter 270, fluid can be delivered from the syringe, through channel, and into the holding space to deploy the implant. FIG. 10 illustrates syringe 276 connected to luer lock 272 such that the syringe and the holding space are in fluid communication.

Figure 11:
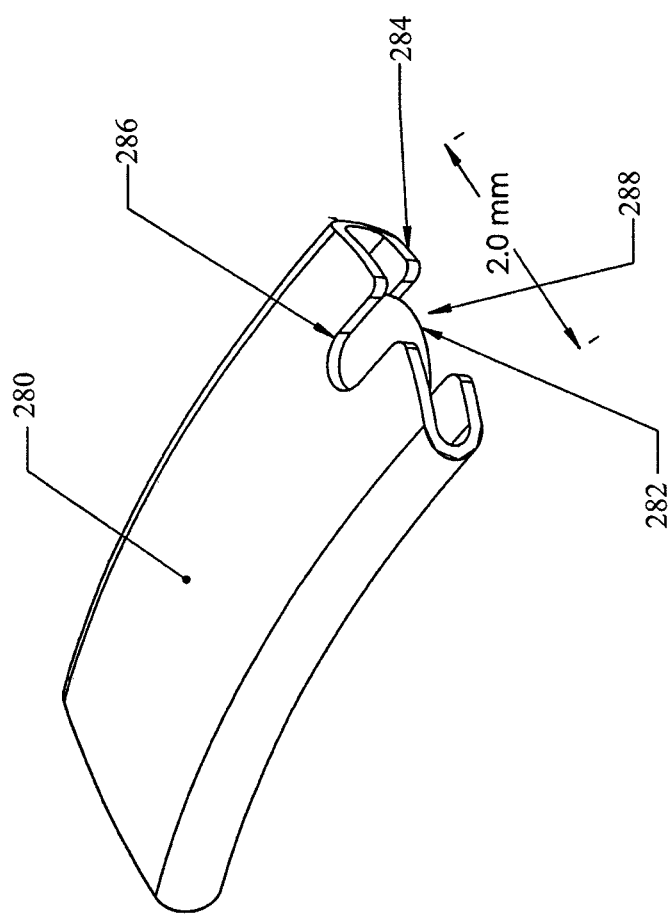
FIGS. 11 and 12 illustrate a distal portion of exemplary inserter with a channel extending therethrough.
Figure 12:
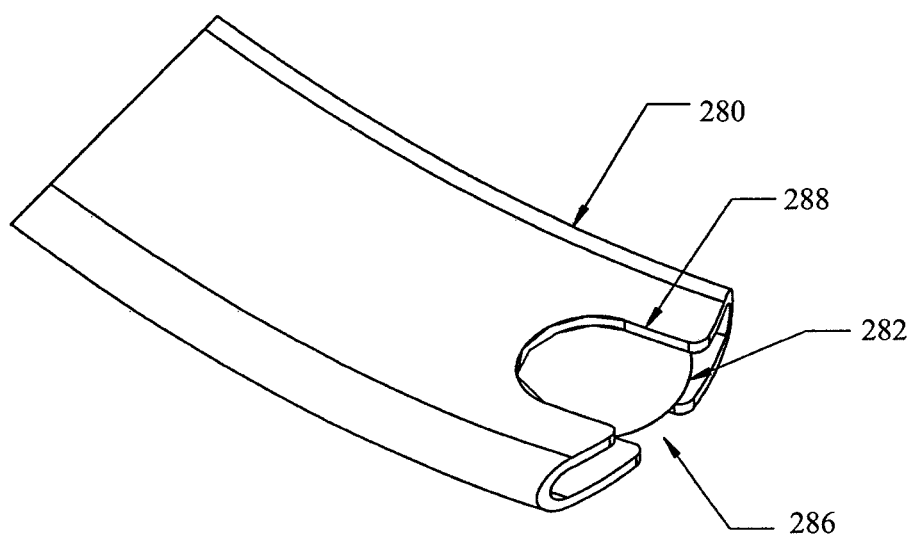

FIGS. 11 and 12 illustrate a distal portion of exemplary inserter 280. In this embodiment the inserter includes cannula or tube 280 configured to house the implant 282 therein. Cannula 280 preferably has a width slightly larger than the width of implant 282. Cannula 280 also preferably has a height that is slightly larger than the thickness of implant 282. The distal end 284 of cannula 280 is preferably shaped to hold implant 282 in a substantially unstressed or non-deformed configuration. Cannula 280 may or may not be slightly curved along its width and/or length to follow the curvature of the cornea. Fluid, e.g., saline or BSS, may be delivered to implant 282 through the channel in the inserter to ensure that implant 282 is hydrated prior to use and/or to release implant 282 from the inserter.

Figure 13:
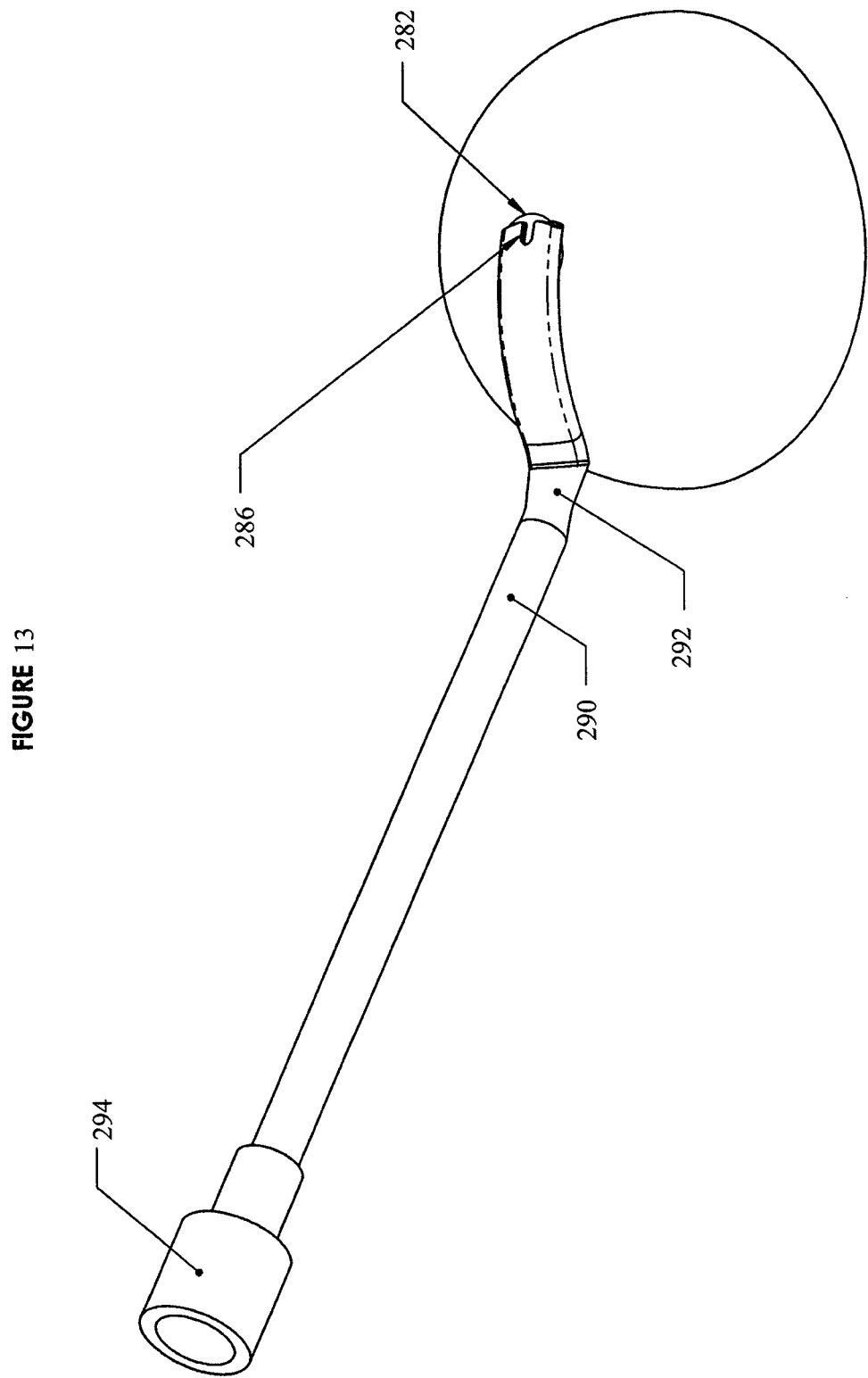
FIG. 13 shows an exemplary inserter, which includes a clearance bend and an elongated portion with an optional luer lock at the proximal end for connecting to a fluid delivering device.

The inserter 280 also includes a top inserter slot 286 through which a surgical cannula, Sinskey Hook, or other tool can be used to hold down implant 282 at the desired location in the cornea as described above. Cannula 280 also includes a bottom opening 288 shown in FIG. 12 through which implant 282 can contact the cornea when the implant is held down as shown in FIG. 13. Preferably, the edges and corners at the tip of cannula 280 are smooth and rounded to avoid damaging the cornea or implant. A handle may be attached to the proximal end of the inserter for easier handling by the user. FIG. 13 shows the entire inserter, which includes a clearance bend 292 and an elongated portion 290 with optional luer lock 294 at the proximal end for connecting a fluid delivering device to the inserter. The fluid delivering device may be coupled to inserter 282 for delivering fluid to the implant through the channel in inserter 282, as is described in more detail herein.

Implant 282 can be implanted in the cornea using any of the procedures described above. In one embodiment a flap is cut into the cornea and lifted to expose a stroma bed of the cornea. The user then positions implant 282 at the desired location using the inserter. When implant 282 is at the desired position, the user can use a surgical cannula or other tool to hold implant 282 through the top inserter slot 286. The user can hold down implant 282 such that the bottom surface of implant 282 contacts the cornea through bottom opening 288. While implant 282 is held down at the desired location, the user retracts the inserter to deposit implant 282 on the cornea. The surgeon can alternatively, or in addition to, deliver fluid to implant 282 through the channel in the inserter to release implant 282 from the holding space. After implant 282 is correctly positioned, the user places the flap back down over implant 282. FIG. 13 shows an example of an inserter positioned over the desired location of the cornea for depositing implant 282 at the desired location.

In some embodiments implant 282 is implanted into a corneal pocket. Cannula 280 is moved to the desired position through the channel that leads to the pocket. The thin cross section of cannula 280 minimizes stress on the cornea as cannula 280 is advanced through the channel to the pocket. When the implant is in position, fluid is delivered from the fluid delivery device, through the cannula, and into the holding space to thereby deploy the inlay out of the holding space and onto the corneal tissue. In alternative embodiments a second channel can also be cut into the cornea to provide access for a surgical tool that can be used to hold down implant 282 to further assist removing the implant from the holding space, as is described in more detail above.

Figure 14:
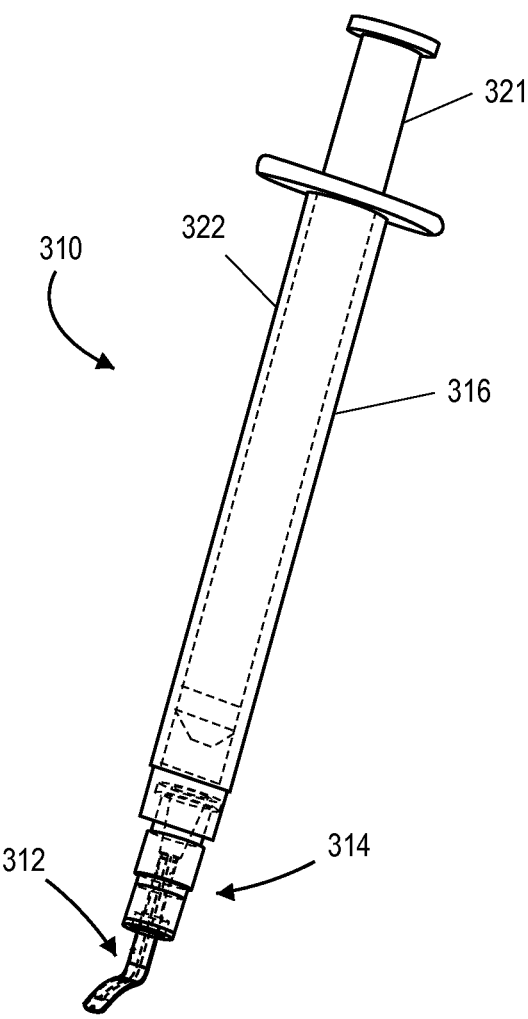
FIG. 14 illustrates an exemplary inserter system.
Figure 15:
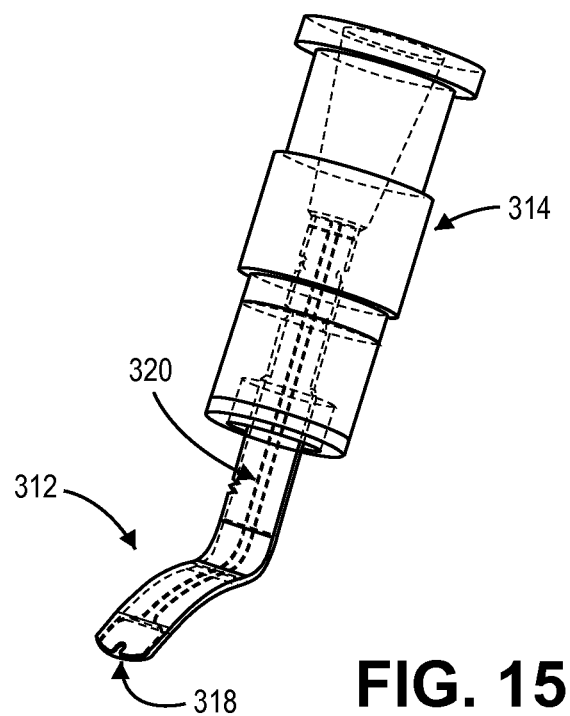
FIG. 15 illustrates the system from FIG. 14 without the fluid delivery device.

FIG. 14 illustrates an exemplary inserter system including inserter 312 secured to hub 314, which is secured to syringe 316 (or any other suitable fluid delivery device). The syringe 316, hub 314, and inserter 312 are all in fluid communication. FIG. 15 illustrates the system without the syringe, showing hub 314 and inserter 312. The proximal end of the hub has a luer lock adapted to securingly couple with a luer lock on the distal end of the syringe. The distal region of inserter 312 has holding space 318 adapted to house the corneal implant therein, which is retained in the holding space by capillary forces, as described above. Inserter 312 has a fluid channel 320 therein extending along the length of the inserter. The proximal region of inserter 312 is adapted to be positioned within hub 314, which is adapted to be coupled to syringe 316 (shown in FIG. 14). Hub 314 is configured to position the distal end of the syringe adjacent to the proximal end of inserter 52 and therefore the proximal end of fluid channel 320 within inserter 312. When the syringe is actuated by advancing plunger 321 with respect to outer tube 322, fluid is advanced from the plunger and into fluid channel 320. In this manner fluid in channel 320 gently pushes the corneal implant positioned in the holding space out of the holding space and into the target delivery zone, such as onto corneal tissue.

In some embodiments system 310 is used to deliver the implant after a flap has been created. In some embodiments system 310 is used to deliver the implant into a pocket formed within the cornea. In some methods of use the implant is deployed from the holding space and onto corneal tissue solely by advancing fluid through channel 320 from the syringe. In some embodiments a separate stripping tool can also be used to assist in the removal of the implant from the holding space, as is described above.

Figure 16A:
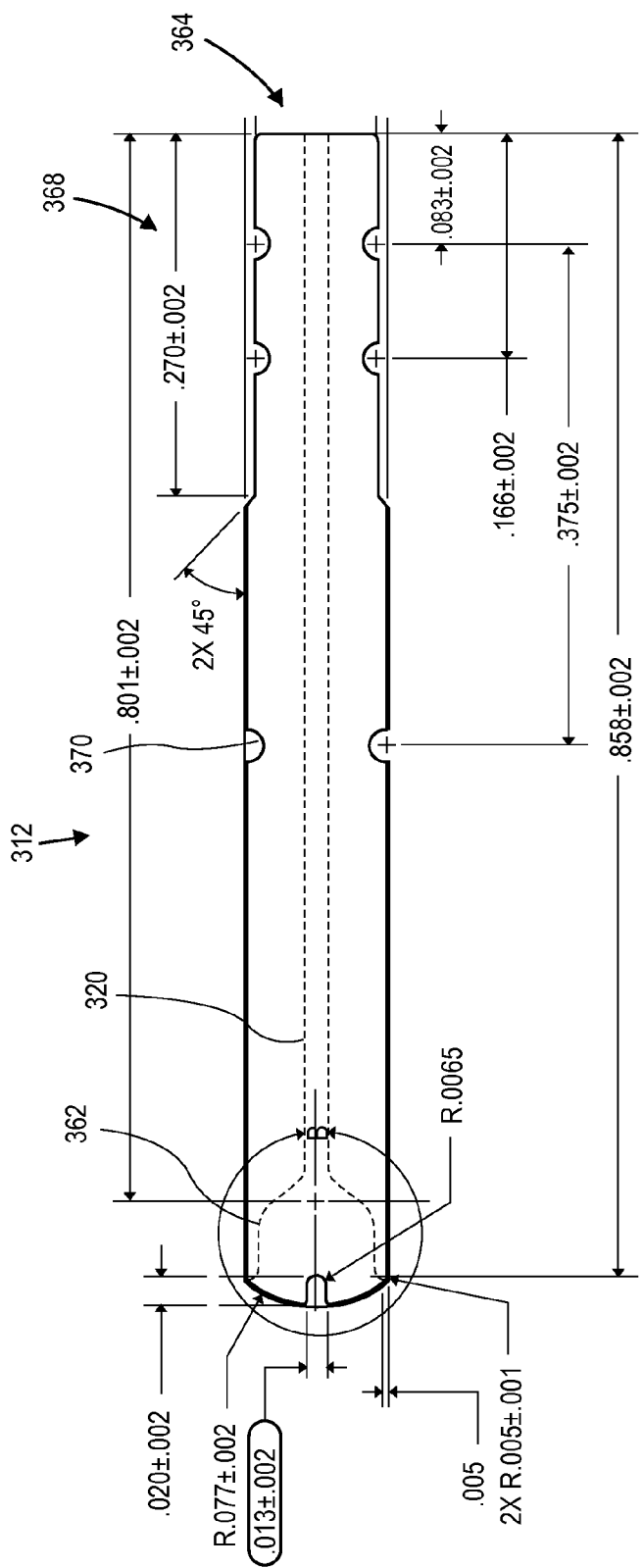
FIGS. 16A-16E illustrate an exemplary inserter.

FIGS. 16A-16E illustrate inserter 312 in a flat configuration prior to any bends being made in the inserter. FIG. 16A shows a top view of inserter 312. Fluid channel 320 is shown in phantom within inserter 312 and extends from proximal end 364 to the holding space in the distal region. The proximal end of the inserter is therefore in fluid communication with the holding space.

The distal end of device 312 could have a different configuration than shown, such as a tear-drop configuration shown above. Proximal region 368 of inserter 312 has a slightly smaller width than the region distal to it, as shown in FIG. 16A. Additionally, inserter 312 includes a plurality of notches 370 formed in the side. While the notches are artifacts of the manufacturing process, the four notches at the proximal end improve the bonding strength between the female hub and the inserter body. To assemble the inserter and the hub, the assembly is glued and the notches are filled in with adhesive, which improves the bond strength. This would also be true if the hub was overlay/insert molded onto the cannula inserter body.

Figure 16B:
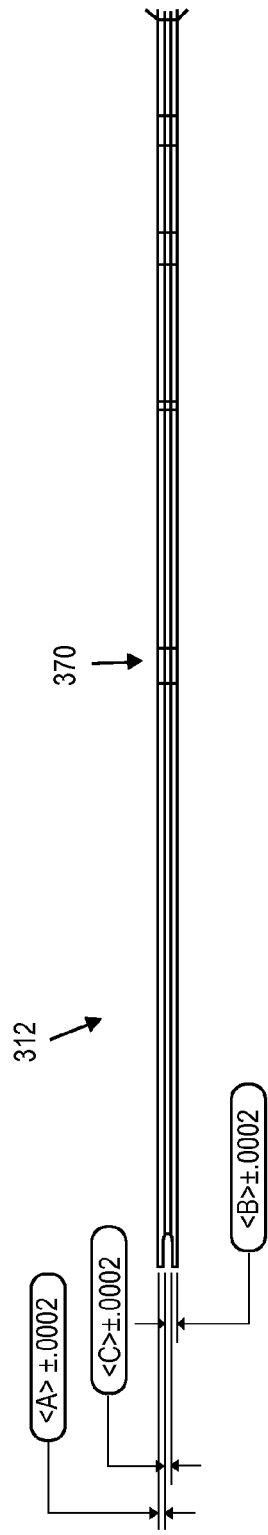
Figure 16C:
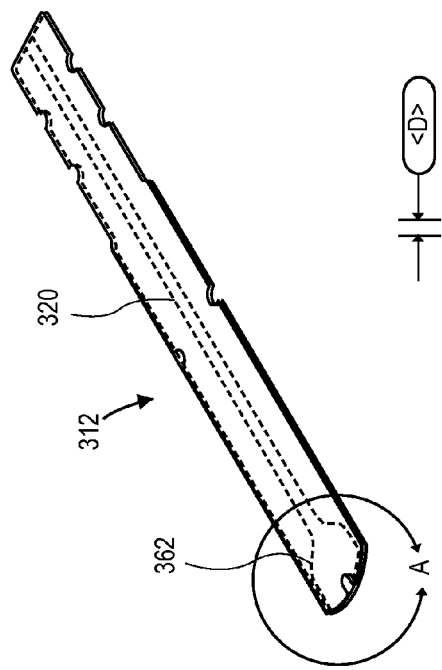
Figure 16E:
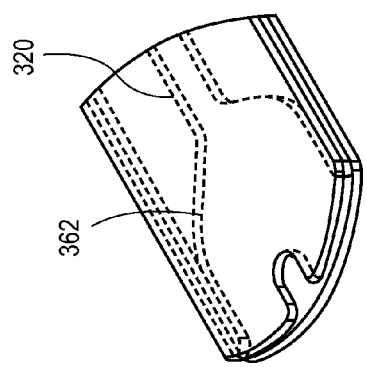
Figure 16D:
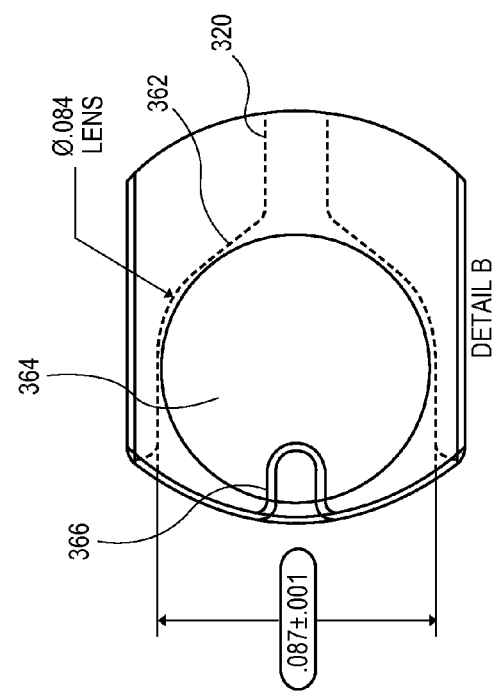

FIG. 16B illustrates a side view of device 312. FIG. 16C illustrates a perspective view of inserter 312. FIG. 16D illustrates a top view of distal section of inserter 312, showing implant 364 disposed in the holding space in a substantially non-deformed configuration. The device also includes top slot 366, but in this embodiment the inserter is not shown with a bottom slot. In alternative embodiments the inserter could have a bottom slot. FIG. 16E illustrates a perspective view of the distal region without the implant disposed in the holding area.

As can be seen, the channel has a width that is less than the maximum width of the holding area. In the distal region of the inserter the side walls that form the channel taper outward and form the larger width holding space. The width of the holding space is such that the implant can be housed therein in a substantially non-stressed configuration, while the smaller width of the channel requires less fluid to be advanced through the inserter to deploy the implant.

Figure 17A:
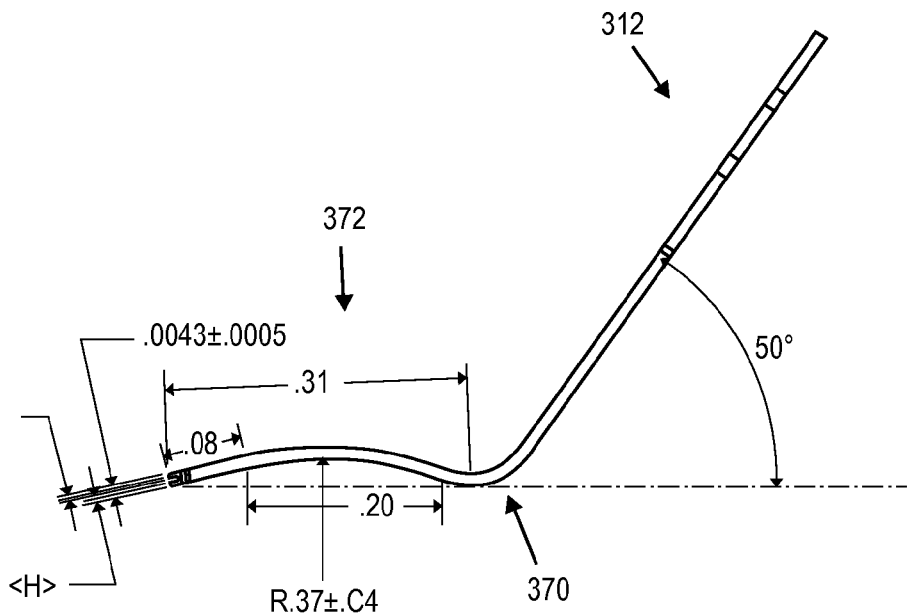
FIGS. 17A-17B illustrate an exemplary inserter.
Figure 17B:
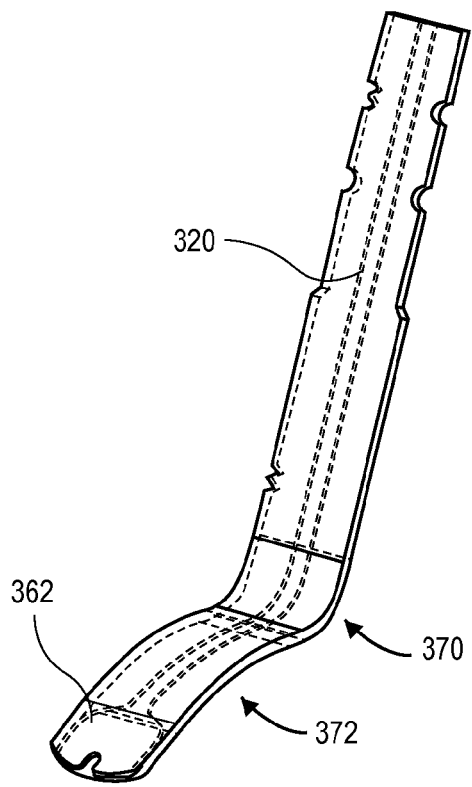

FIGS. 17A and 17B show inserter 312 after bend 370 and optional bend 372 have been formed therein. Of course, bend 72 need not be formed, as is the case in the device shown in FIG. 7A-7E. The device shown in FIGS. 7A-7E could therefore be modified to have a fluid channel therein to allow for a fluid to be delivered through the inserter and into holding space.

In some embodiments herein (such as FIGS. 16A-17B), the holding space maximum width is just slightly larger than the diameter of the corneal implant. For example, in a particular non-limiting embodiment the holding space width is about 2.2 mm, and the diameter of the inlay is about 2.0 mm. This exemplary 0.2 mm difference provides a little clearance for the implant, and the relatively small holding space width allows the outer surfaces of the inserter to be relatively small, which reduces the delivery profile of the inserter. This helps minimize damage to the cornea.

In some embodiments the width of the implant can be between about 1 mm and about 3 mm. By way of additional example, in some embodiments the implant diameter is about 1 mm and the holding space maximum width is about 1.2 mm. In alternative exemplary embodiments the implant diameter is about 3.0 mm and the holding space width is about 3.2 mm.

In some embodiments the height of the implant, which can also be considered the "thickness" of the implant is between about 10 microns and about 50 microns. The height of the holding space is just slightly larger than the height of the implant. For example, in some embodiments the implant height, or thickness, is between about 20 microns and about 40 microns, and the respective holding space height is between about 22 microns and about 50 microns. In some embodiments the implant height is about 30 microns and the holding space height is about 35 microns. Again, in these embodiments the relatively small height of the holding space (and the overall height of the distal portion of the inserter) reduces the delivery profile and minimizes damage to the cornea.

As shown in FIGS. 16A-16E, the maximum width of the inserter channel is less than the maximum width of the holding space. The can help allow for a very small volume of fluid to be advanced through the channel towards the holding space to deploy the implant from the holding space. Specifically, the maximum width of the inserter channel is shown as less than half of the maximum width of the holding space. In some embodiments the channel maximum width can be less than or equal to half the maximum width of the holding space.

In the embodiment shown in FIGS. 16A-17B, the channel extends all the way from the holding space to the proximal end of the inserter elongate body.

Figure 18A:
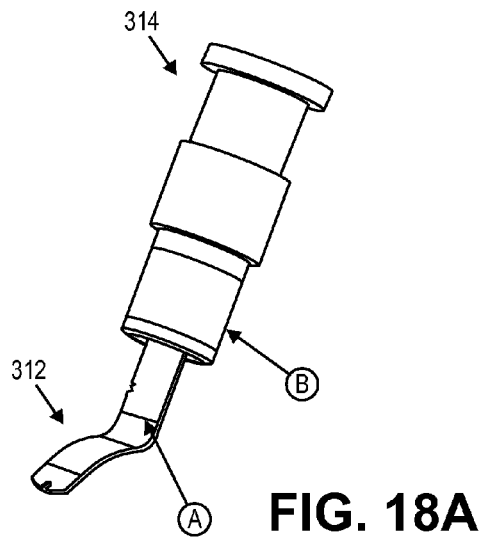
FIGS. 18A-18D illustrate views of an exemplary hub secured to an exemplary inserter.
Figure 18B:
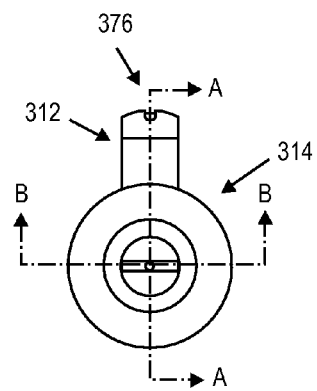
Figure 18C:
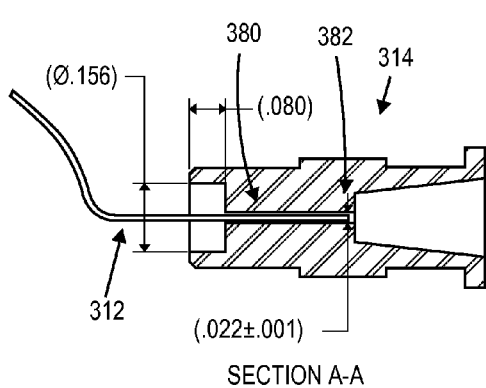

FIGS. 18A-18D illustrate views of hub 314 secured to inserter 312 (the syringe is not shown for clarity). The proximal end of inserter 314 is disposed within the distal end of hub 314. FIG. 18A illustrates a perspective view of the assembly. FIG. 18B illustrates an end view viewing the open end of hub 314. Fluid channel 320 in inserter 312 can be seen therein. The distal end 376 of inserter 312 can also be seen. FIG. 18C shows section A-A from FIG. 18B, a cross sectional side view showing a proximal region of inserter 312 positioned within an internal channel 380 of hub 314.

Figure 18D:
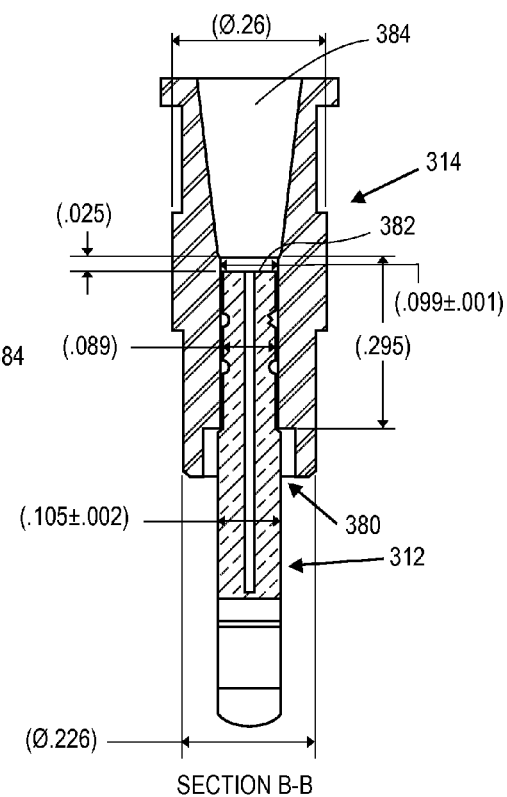

Hub 314 also includes stop 382 which prevents inserter 312 from being advanced too far proximally within hub 314. Stop 382, however, has a bore therein to allow proximal chamber 384 of the hub to be in fluid communication with fluid channel 320 within inserter 312. FIG. 18D illustrates section B-B from FIG. 18B, showing inserter 312 disposed within channel 380 in hub 314.

Figure 19A:
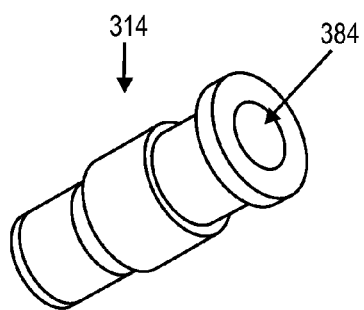
FIGS. 19A-19D illustrate views of the hub from FIGS. 18A-18D.
Figure 19B:
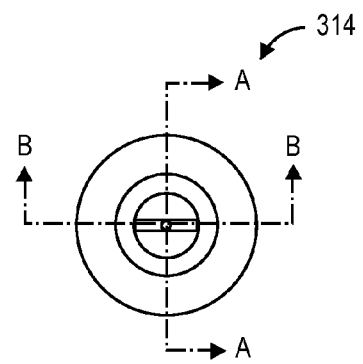
Figure 19C:
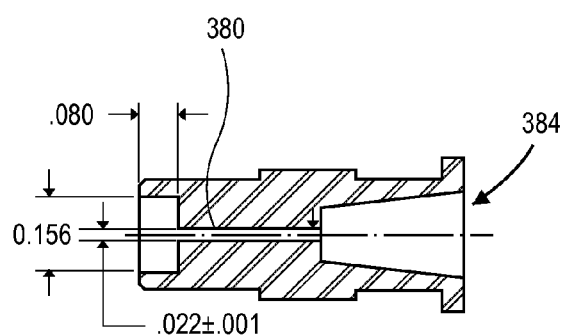
Figure 19D:
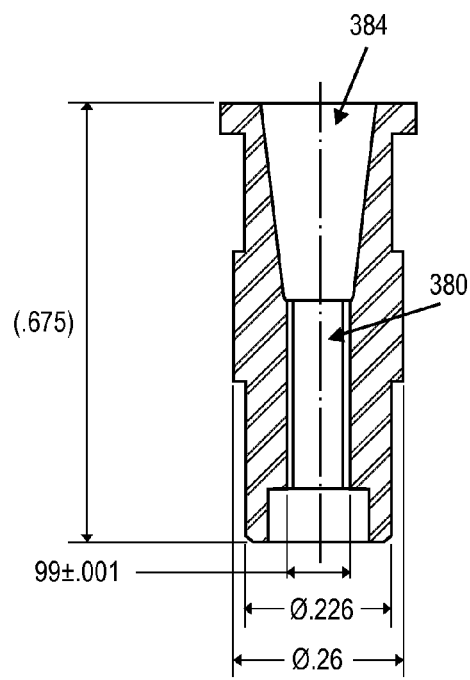

FIGS. 19A-19D illustrate views of hub 314 not coupled to an inserter or to a fluid delivery device (such as a syringe). FIGS. 19A-19D correspond to the figures in FIGS. 18A-18D but without inserter 312. FIG. 19A shows the proximal end including proximal chamber 834 adapted to receive a syringe or other fluid delivery device therein. FIG. 19B shows an end view from the proximal end of hub 314. FIGS. 19C and 19D illustrate sectional views with channel 380 which is adapted to receive an implant inserter therein.

When delivering a corneal inlay onto corneal tissue using fluid (whether or not a separate tool is also used to assist in the delivery), the amount of fluid delivered onto the cornea can influence the procedure. For example, it is generally not beneficial to deliver a relatively large volume of fluid onto the cornea because it will take a longer period of time for a larger volume of fluid to evaporate (or dissipate if within the cornea), which increases the time it takes for the implant to adhere to the corneal bed. A relatively large volume of fluid can also make visualizing the implant more difficult and makes it difficult to control the position of the implant relative to the pupil. Conversely, providing too little fluid can cause the implant to stick to the stroma and surgical instruments and can therefore be difficult to move and reposition.

Additionally, it is generally desirable to minimize the pressure on the corneal tissue bed to prevent damage to the eye. It is therefore generally important to carefully control the amount of fluid that is pushed out of the inserter system to deliver the corneal implant. In some embodiments between about 0.5 to about 2.0 microliters of saline are advanced into the fluid channel within the delivery device. This range is not, however, intended to be strictly limiting. For example, about 5 microliters could be used as well. In some embodiments between about 0.5 and about 1.0 microliters of fluid are advanced. In some embodiments between about 1.0 and about 2.0 microliters are used. In some embodiments, however, more fluid can be delivered, and the excess fluid could simply be aspirated or removed. The inserter bodies described herein can hold approximately between about 0.5 and about 4.0 microliters, but in other embodiments the inserters can be modified to hold more or less fluid.

Figure 20A:
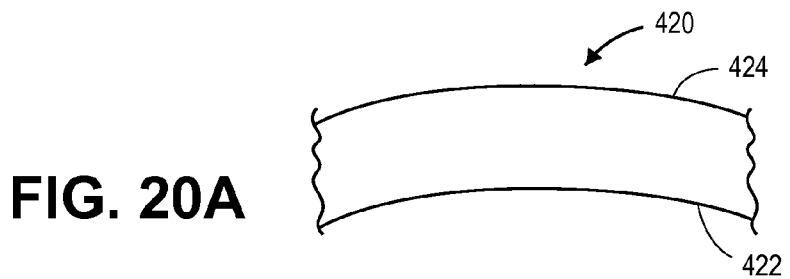
FIGS. 20A-20F show side views illustrating an exemplary method of inserting a corneal inlay into a corneal pocket created within the cornea from within an exemplary inserter.
Figure 20B:
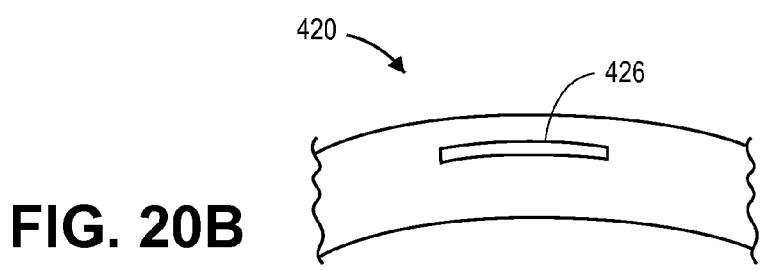

FIGS. 20A-20F show side views illustrating an exemplary method of inserting a corneal inlay into a corneal pocket created within the cornea from within inserter 312. FIG. 20A illustrates an exemplary cornea 420 into which the inlay is going to be positioned. Cornea 420 has an anterior surface 424 and posterior surface 422. FIG. 20B illustrates pocket 426 that has been created in cornea 420. The corneal pocket is created to be able to receive the corneal implant therein. The pocket is created to have substantially the same shape and dimensions of the corneal implant to be positioned in the pocket.

Figure 20C:
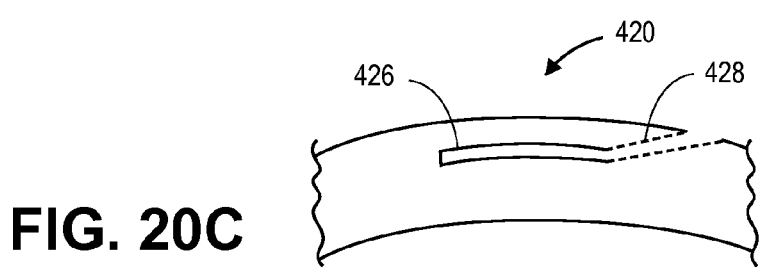

Pocket 426 can be created by known methods, such as by focusing a laser beam at corneal tissue, and moving the laser beam throughout the region of corneal tissue that is to be removed or separated to form the pocket. The laser beam disrupts the corneal tissue, forming a pocket with the desired shape and dimensions. As shown in FIG. 20C, channel 428 is then created to allow access to the created pocket 426 from outside the cornea. Channel 428 connects the space outside the cornea with pocket 426, thereby creating a path for inserter 312 to follow to access the pocket. Channel 428 can be made with a laser beam in the same or similar manner in which pocket 426 is created. A surgical knife can also be used to create access channel 428. Debris and gas bubbles created during the pocket and channel formation can then be aspirated if necessary.

Figure 20D:
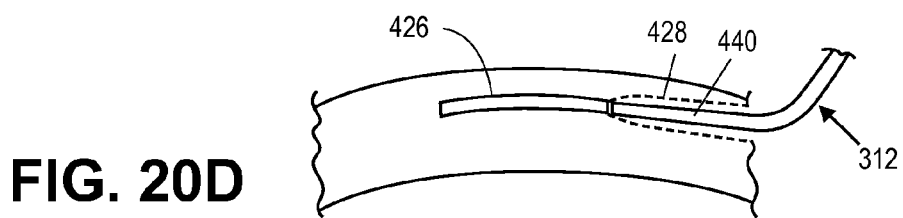
Figure 20E:
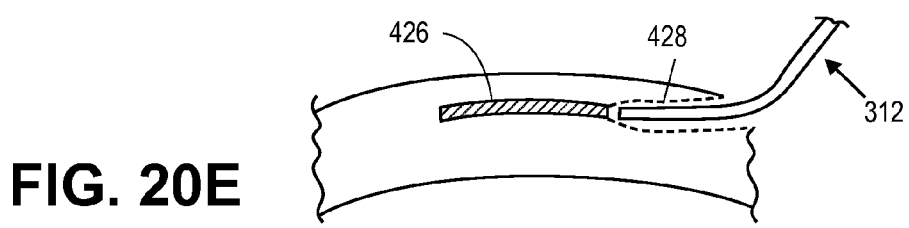
Figure 20F:
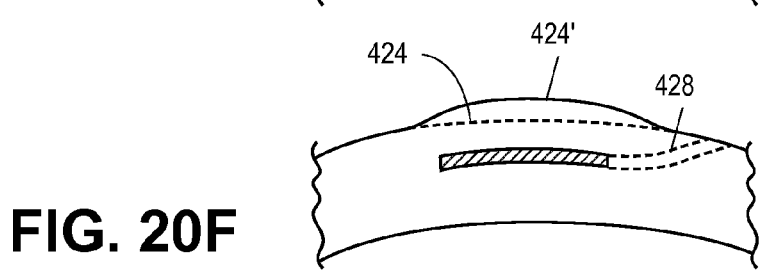

As shown in FIG. 20D, inserter 312, with the inlay disposed therein in the holding space (not shown) is advanced into channel 428 and the distal end of inserter 440 is positioned adjacent pocket 426. The hub and fluid delivery device are not shown for clarity. Fluid is then advanced through the channel within the inserter 312 using the fluid delivery device (e.g., syringe), which gently pushes inlay 444 from the holding space and into the pocket, as shown in FIG. 20E. Inserter 312 is then removed from the cornea, leaving the inlay positioned within the cornea. Channel 428 will eventually heal over time. FIG. 20F also illustrates an exemplary change in curvature of the anterior surface of the cornea, from first shape 424 to second shape 424'. The increase in curvature is in the central region of the pupil, while a region in the periphery of the pupil remains unchanged. The central region is therefore created to create near vision, while the peripheral region allows for distance vision. The inlay in this embodiment is therefore adapted to correct presbyopia by creating near vision in the center of the pupil but allowing distance vision in a region peripheral to the central region.

In alternative embodiments, a secondary channel, in addition to channel 428, can also be created that creates a secondary access location to the pocket. The secondary channel accesses the pocket from a direction other than channel 428. The secondary channel can be created in the same way as channel 428. The secondary channel can be substantially on the opposite side of the cornea (i.e., substantially 180 degrees away from) relative to channel 428. The secondary channel allows a path for a tool to be advanced into the pocket and assist in the removal of the implant from the holding space. Using a tool in this manner is described in more detail above.

What is claimed is:

1. A corneal implant inserter apparatus, comprising:
   a corneal implant;
   a holding space at a distal end of an elongate body, wherein the holding space is adapted to house the corneal implant therein in a substantially unstressed configuration, the elongate body comprising a distal port out of which the corneal implant passes when deployed from the holding space, the distal port having a width greater than a diameter of the corneal implant;
   a fluid disposed in the holding space such that the corneal implant is retained within the holding space due to a surface tension of the fluid; and
   a channel extending within the elongate body such that the channel is in fluid communication with the holding space.

2. The apparatus of claim 1, wherein the holding space has a generally flat top and a generally flat bottom.

3. The apparatus of claim 1, wherein the channel extends from the holding space to a proximal end of the elongate body.

4. A corneal implant inserter apparatus, comprising:
   a corneal implant;
   an elongate body comprising a distal holding space in fluid communication with a channel extending through the elongate body, the elongate body comprising a distal port out of which the corneal implant passes when deployed from the holding space, the distal port having a width greater than a diameter of the corneal implant, wherein the holding space has a generally flat top and a generally flat bottom;

a corneal implant retained in the holding space between the generally flat top and the generally flat bottom; and a fluid disposed in the holding space such that the corneal implant is retained within the holding space due to a surface tension of the fluid.

5. The apparatus of claim 4, wherein the corneal implant is retained in the holding space in a substantially unstressed configuration.

6. The apparatus of claim 4, wherein the channel extends from the holding space to a proximal end of the elongate body.

7. A corneal implant inserter system, comprising:
a corneal implant;
a corneal implant inserter comprising a channel fluidly connecting a holding space in a distal portion of the inserter and a proximal end of the corneal implant inserter, the corneal implant inserter comprising a distal port out of which the corneal implant passes when deployed from the holding space, the distal port having a width greater than a diameter of the corneal implant;
a fluid disposed in the holding space such that the corneal implant is retained in the holding space due to a surface tension of the fluid; and
a fluid delivery device adapted to be positioned relative to the corneal implant inserter such that it is in fluid communication with the corneal implant inserter channel such that fluid can be delivered from the fluid delivery device into the channel to deploy the corneal implant from the holding space.

8. A method of deploying a corneal implant onto corneal tissue, comprising:
providing a corneal implant inserter with a corneal implant retained in a holding space in a substantially unstressed configuration in a distal region of the inserter, the corneal implant inserter comprising a distal port, the distal port having a width greater than a diameter of the corneal implant; and
delivering fluid from a delivery device into a channel extending through the corneal implant inserter, wherein the channel is in fluid communication with the holding space, and wherein delivering the fluid deploys the corneal implant from the holding space through the distal port, and onto corneal tissue.

9. The method of claim 8, further comprising creating a corneal flap and lifting the flap to expose the corneal tissue prior to the delivering step.

10. The method of claim 8, further comprising applying a force on the corneal implant with a tool to assist in deploying the corneal implant from the holding space.

11. The method of claim 10, wherein applying a force on the corneal implant with a tool comprises positioning the tool in a slot formed in a top portion of the holding space.

12. The method of claim 8, further comprising, prior to the delivering step:
creating a corneal pocket within the cornea;
creating an access channel to the pocket; and
advancing the holding space into the access channel and towards the pocket.

13. The method of claim 8 further comprising:
creating a second access channel to the pocket;
positioning a tool in the second access channel; and
applying a force on the corneal implant with the tool to assist in deploying the corneal implant from the holding space.

14. A corneal implant inserter apparatus, comprising:
an elongate body with a distal region, and a corneal implant retained at the distal region in a substantially unstressed configuration due to surface tension of a fluid, the elongate body comprising a distal port out of which the corneal implant passes, the distal port having a width greater than a diameter of the corneal implant; and
a fluid channel extending within the elongate body such that the channel is in fluid communication with the distal region.

15. A method of deploying a corneal implant onto corneal tissue, comprising:
providing an elongate body with a distal region, and a corneal implant retained at the distal region in a substantially unstressed configuration due to a surface tension of a fluid, the distal region comprising a distal port from which the corneal implant is deployed, the distal port having a width greater than a diameter of the corneal implant; and
delivering fluid through a fluid channel in the elongate body to deploy the corneal implant from the distal region and out of the distal port, and onto corneal tissue.

* * * * *